United States Patent [19]

Kaufman et al.

[11] Patent Number: 5,036,462
[45] Date of Patent: Jul. 30, 1991

[54] INTERACTIVE PATIENT ASSISTANCE AND MEDICATION DELIVERY SYSTEMS RESPONSIVE TO THE PHYSICAL ENVIRONMENT OF THE PATIENT

[75] Inventors: Stephen B. Kaufman, Highland Park; Aleandro DiGianfilippo, Crystal Lake; Tamara L. Sager, Libertyville; Alan R. Meyer, North Riverside, all of Ill.

[73] Assignee: Healthtech Services Corp., Northbrook, Ill.

[21] Appl. No.: 414,705

[22] Filed: Sep. 29, 1989

[51] Int. Cl.$^5$ .......................... G06F 15/42; A61J 1/03; B65D 83/04
[52] U.S. Cl. .................................. 364/413.01; 221/9; 221/12; 364/479; 364/413.02
[58] Field of Search ...................... 364/413.02, 413.01, 364/479; 221/2, 9, 12

[56] References Cited

U.S. PATENT DOCUMENTS

| | | | |
|---|---|---|---|
| 3,369,697 | 2/1968 | Glucksman et al. | 221/9 |
| 3,395,829 | 8/1968 | Cogdell et al. | 221/15 |
| 3,651,984 | 3/1972 | Redenbach | 221/3 |
| 3,722,739 | 3/1973 | Blumberg | 221/3 |
| 3,743,181 | 7/1973 | Bentley | 236/44 R |
| 3,762,601 | 10/1973 | McLaughlin | 221/2 |
| 3,815,780 | 6/1974 | Bauer | 221/15 |
| 3,857,383 | 12/1974 | Sommerfeld et al. | 128/630 |
| 3,911,856 | 10/1975 | Ewing | 206/534 |
| 3,917,045 | 11/1975 | Williams et al. | 194/210 |
| 3,964,638 | 6/1976 | Dimauro | 221/3 |
| 3,968,900 | 7/1976 | stambuk | 221/3 |
| 3,998,356 | 12/1976 | Christensen | 221/2 |
| 4,034,740 | 7/1977 | Atherton et al. | 600/22 |
| 4,034,757 | 7/1977 | Glover | 604/404 |
| 4,130,881 | 12/1978 | Haessler et al. | 364/900 |
| 4,207,992 | 6/1980 | Brown | 221/15 |
| 4,223,801 | 9/1980 | Carlson | 221/3 |
| 4,227,526 | 10/1988 | Goss | 604/5 |
| 4,258,354 | 3/1981 | Carmon et al., | 340/309.4 |

(List continued on next page.)

OTHER PUBLICATIONS

Comerchero, H. et al. "SOLO: An Interactive Microcomputer-Based Bedside Monitor", 1979.

"Automatic Feedback Instrumentation for Hospital Room Utilizing Microsensors", *IBM Technical Disclosure Bulletin*, vol. 29, No. 3, Aug. 1986, 1320.

Comerchero, H. et al., "A Micro-Computer Based System for the Management of the Critically Ill", 1978.

Blum, B. et al., "Protocol Directed Patient Case Using a Computer", 1980.

Rodbard, D. et al., "*A Data Management Program to Assist with Home Monitoring of Blood Glucose and Self Adjustment of Insulin Dosage for Patient with Diabetes Mellitus and their Physicians*", 1984.

Kouchoukos, N. T. et al., "Automated Patient Care Following Cardiac Surgery", *Cardiovasc. Clin.* vol. 3, No. 3, 1971, 109-20.

Hudson, D. L. et al., "*Microcomputer-Based Expert System for Clinical Decision-Making*", 1981.

Worthman, L. G. et al., "Quality Assessment in Emergency Medical Services Systems: The Criteria Mapping Method", 1979.

Greefield et al., "*The Clinical Investigation and Manage-*

(List continued on next page.)

Primary Examiner—Clark A. Jablow
Attorney, Agent, or Firm—Fuller, Ryan & Hohenfeldt

[57] ABSTRACT

A medication delivery device measures a preselected physical parameter of a patient as well measures at least one preselected parameter in the patient's immediate environment that relates to the physical parameter. A control element compares the preselected physical parameter measured with the preselected environmental parameter measured. A first command signal is generated when a predetermined correlation exists between the two parameters, while a second command signal is generated when it does not. The command signal can be used to base a decision to dispense medication to the patient, or to change the patient's immediate environment.

14 Claims, 20 Drawing Sheets

U.S. PATENT DOCUMENTS

| | | | |
|---|---|---|---|
| 4,275,384 | 6/1981 | Hicks et al. | 340/309.4 |
| 4,360,125 | 11/1982 | Martindale et al. | 221/2 |
| 4,361,408 | 11/1982 | Wirtschafter | 368/10 |
| 4,367,955 | 1/1983 | Ballew | 368/10 |
| 4,382,688 | 5/1983 | Machamer | 368/10 |
| 4,419,016 | 12/1983 | Zoltan | 368/10 |
| 4,448,541 | 5/1984 | Wirtschafter | 368/10 |
| 4,473,884 | 9/1984 | Behl | 364/479 |
| 4,483,626 | 11/1984 | Noble | 368/10 |
| 4,490,711 | 12/1984 | Johnston | 340/309.4 |
| 4,504,153 | 3/1985 | Schollmeyer et al. | 368/10 |
| 4,526,474 | 7/1985 | Simon | 368/10 |
| 4,572,403 | 2/1986 | Benaroya | 221/3 |
| 4,573,606 | 3/1986 | Lewis et al. | 221/2 |
| 4,616,316 | 10/1986 | Hanpeter et al. | 364/413.02 |
| 4,674,651 | 6/1987 | Schidmore et al. | 221/3 |
| 4,674,652 | 6/1987 | Aten et al. | 221/3 |
| 4,695,954 | 9/1987 | Rose et al. | 364/413.01 |
| 4,712,562 | 12/1987 | Ohayon et al. | 128/672 |
| 4,725,997 | 2/1988 | Urquhart et al. | 368/10 |
| 4,731,726 | 3/1988 | Allen III. | 364/413.09 |
| 4,776,016 | 10/1988 | Hansen | 381/42 |
| 4,803,625 | 2/1989 | Fu et al. | 364/413.03 |
| 4,839,806 | 6/1989 | Goldfischer et al. | 364/413.02 |
| 4,933,873 | 6/1990 | Kaufman et al. | 364/513.5 |
| 4,942,544 | 7/1990 | McIntosh et al. | 364/413.02 |

OTHER PUBLICATIONS ment of Chest Pain in an Emergency Department", *Medical Care*, vol. 15, No. 11, Nov. 1977, 989–905.

Sanders, S. J. et al. "Micro-Computer Controlled Care System for the Severely Physically Impaired", 1984.

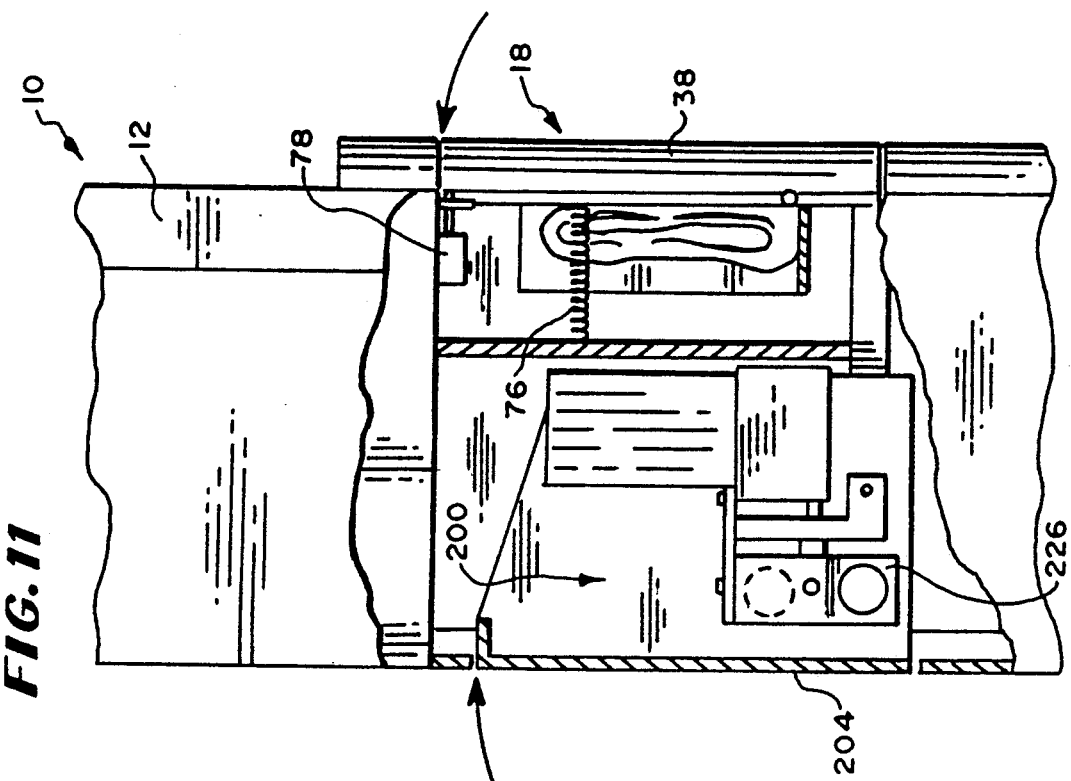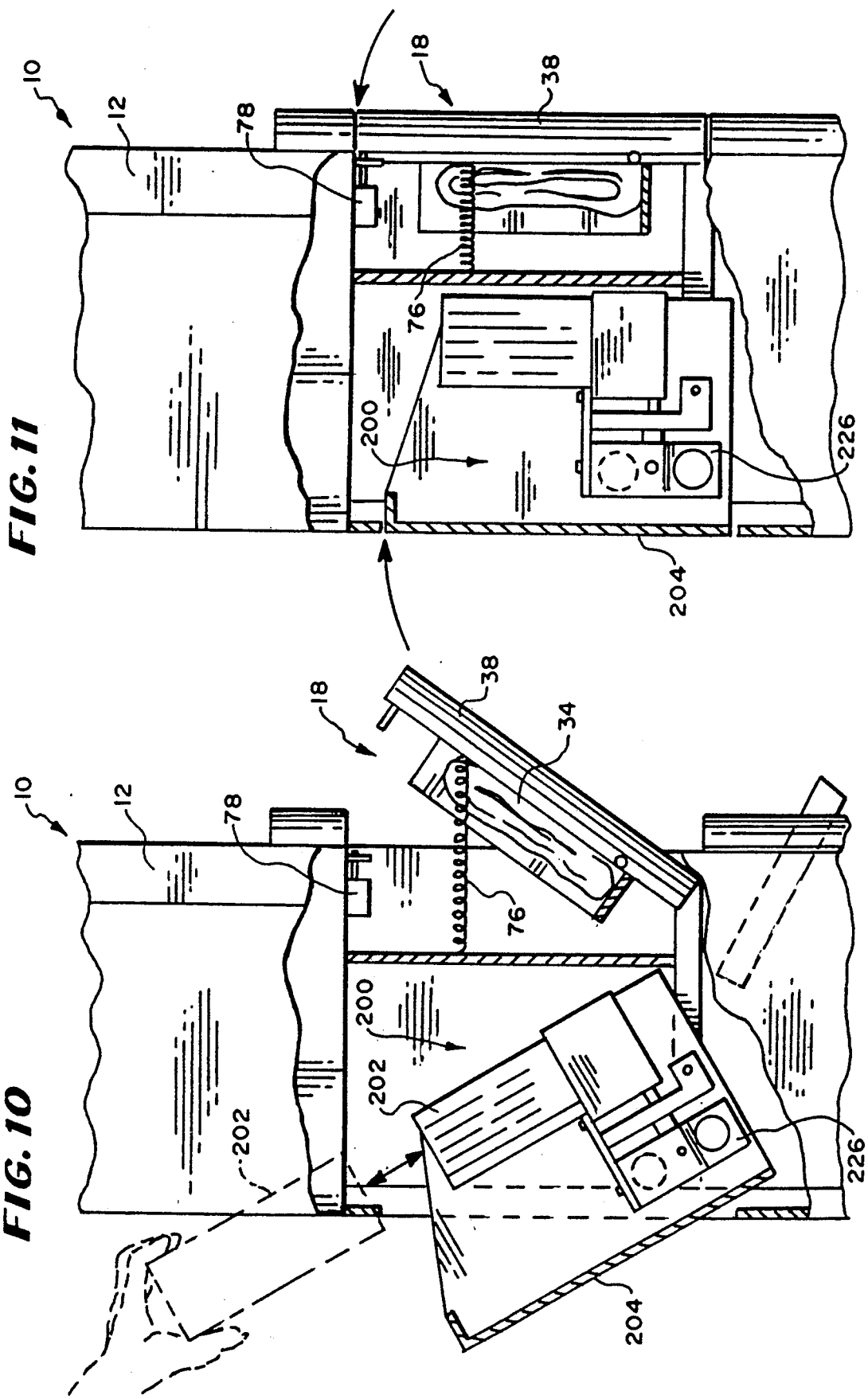

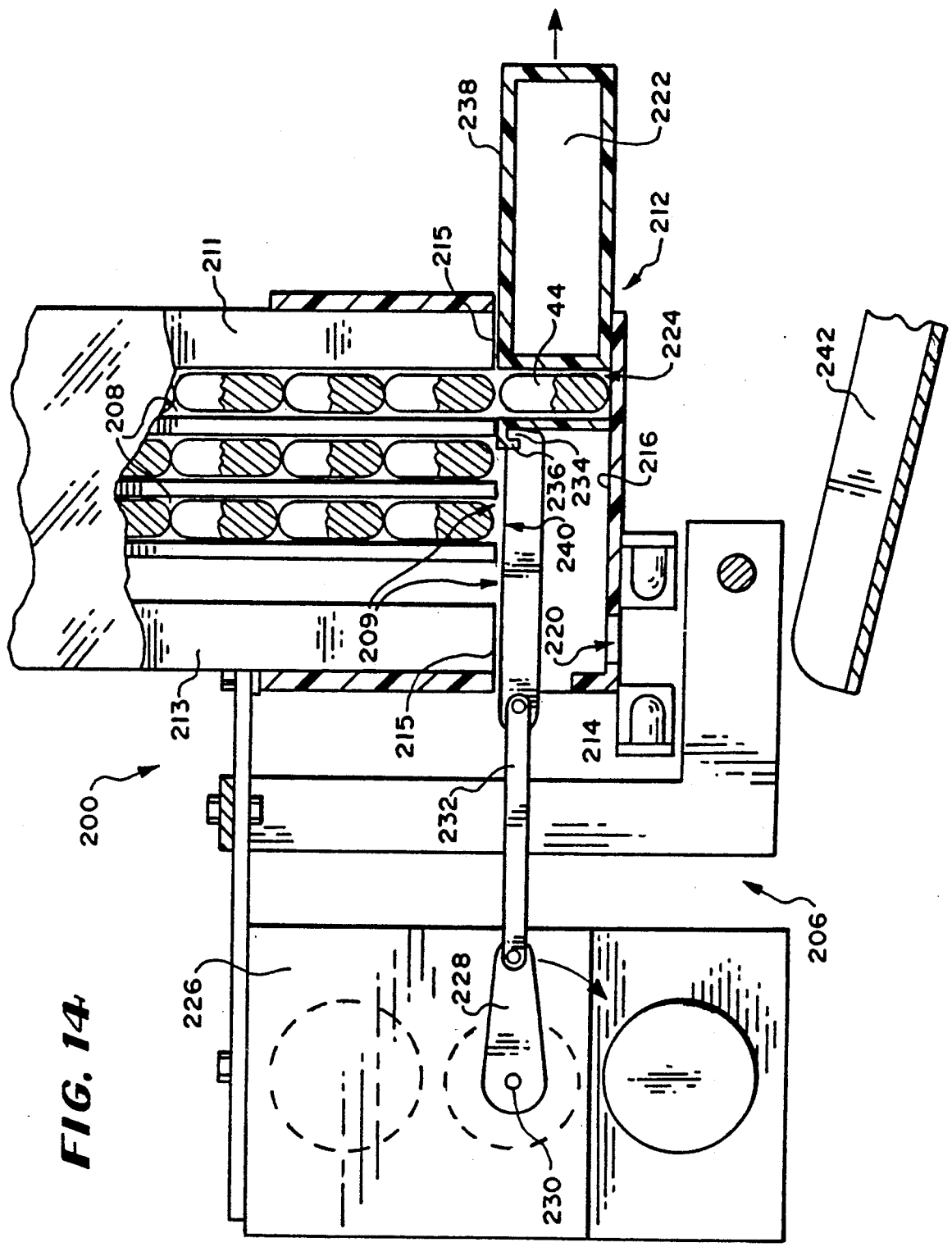

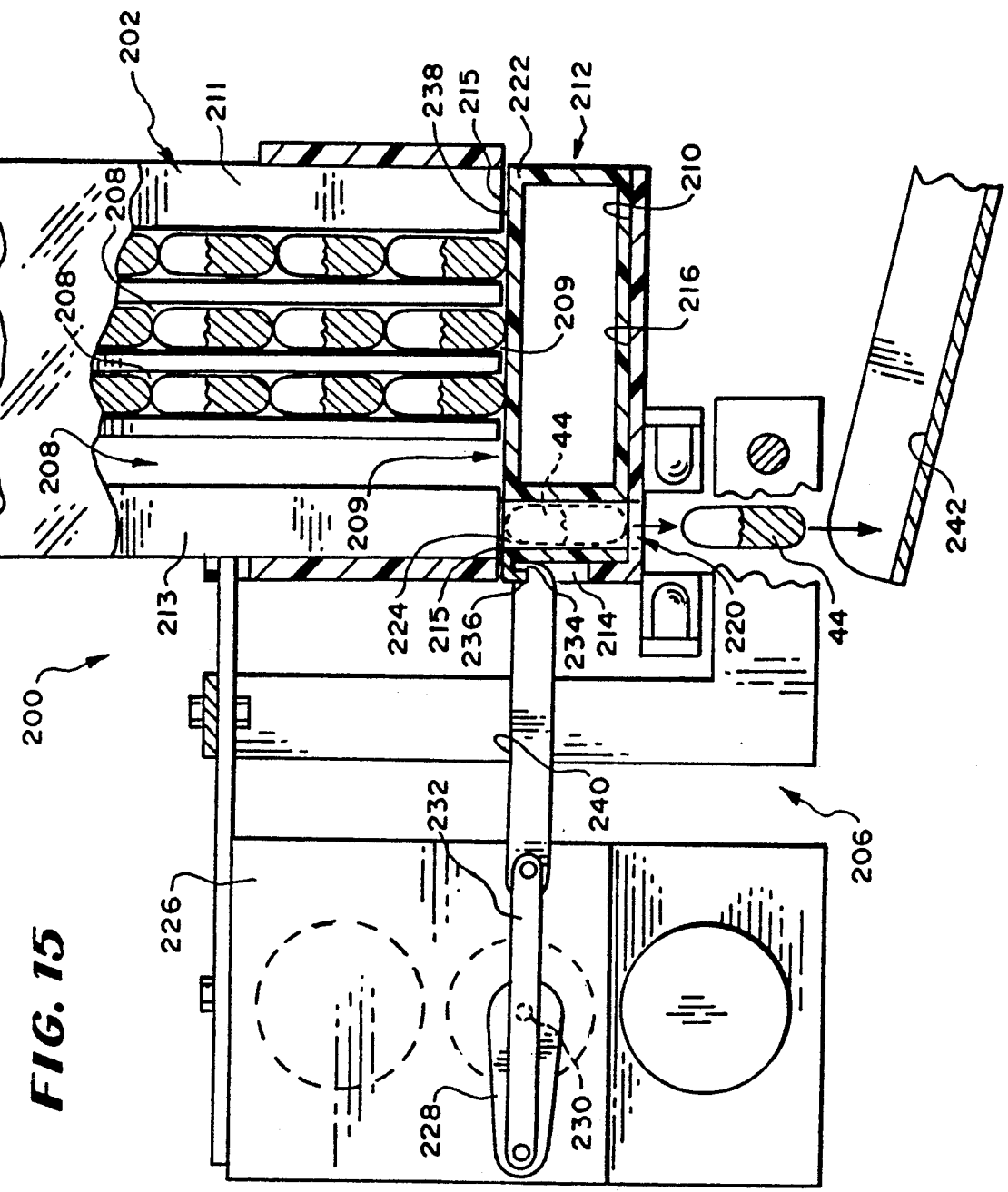

INTERACTIVE PATIENT ASSISTANCE AND MEDICATION DELIVERY SYSTEMS RESPONSIVE TO THE PHYSICAL ENVIRONMENT OF THE PATIENT

FIELD OF THE INVENTION

The invention generally relates to systems for dispensing medications. In a more particular sense, the invention concerns systems which oversee and coordinate the administration of complex medication regimens at home, outside the support system of a hospital or pharmacy, and without the day to day supervision of medical personnel. In this more particular sense, the invention also concerns automated home care patient health monitoring systems.

BACKGROUND OF THE INVENTION

Due to advances in medicine and medical treatments in general, people are living longer. As a result, the number and percentage of older people are growing in the United States and elsewhere.

However, despite medical advances, many elderly people still face chronic and debilitating health problems. Arthritis, hypertension, and heart conditions are but a few examples of the problems associated with longevity.

Treatment of these health problems often requires close compliance with relatively complex medication regimes. It is not unusual for a person having one of the above health problems to be taking four or more different prescription drugs at one time. These drugs often differ significantly in dosages, both as to time and amount, as well as in their intended physiological effects. These drugs also often differ in the severity of potentially adverse reactions due to mismedication.

Close and careful compliance with these complex medication regimes is a difficult task in itself. The difficulty is greatly enhanced, considering that the elderly must discipline themselves to follow these regimes at home, without the day-to-day support and supervision of trained hospital and pharmacy personnel, and often without the day-to-day support and supervision of their immediate families or other caregivers. Furthermore, a loss in short term memory can be naturally attributed to the aging process and to the medication themselves, resulting in forgetfulness and further confusion in scheduling compliance with complicated medication regimes.

The elderly are therefore increasingly at risk of hospitalization or death from mismedication.

An interactive patient assistance device, ideally suited to the needs of home care patients—young and old alike—is described in Kaufman et al. U.S. patent application Ser. No. 201,779 (filed June 2, 1988), now U.S. Pat. No. 4,933,873. The device includes a self-contained medication delivery mechanism and self-contained physical testing apparatus. The device normally retains the medication and the testing apparatus away from access by the patient. Both medication and the testing apparatus are made available to the patient, either in response to a prescribed schedule or in response to a verbal command made by the patient.

The present invention enhances and expands the flexible, interactive system described in the Kaufman et al. application.

The invention is directed to improving the overall well-being and lifestyle of home care patients who are on complicated medication regimes. The invention addresses the problems of compliance with a complicated regime of differing medications and solves these problems by providing a reasonable degree of self-sufficiency and personal control over the administration of medication without sacrificing the overall therapeutic objectives of the prescribed medical treatment.

SUMMARY OF THE INVENTION

One aspect of the invention provides a medication delivery device that includes a medication delivery mechanism for storing at least one dose of medication and for selectively making the medication dose available to the user or patient. The device also includes a physical testing apparatus usable by the patient for measuring a preselected physical parameter. In accordance with the invention, the device also includes a testing apparatus for sensing at least one preselected parameter in the patient's immediate environment.

A control element associated with the device compares the measured preselected physical parameter with the measured preselected environmental parameter. The control element generates a first command signal when a predetermined correlation exists between the two parameters and generates a second command signal when the predetermined correlation is absent. A first output is generated in response to the first command signal, while a second output, different from the first output, is generated in response to the second command signal.

In accordance with this aspect of the invention, one of these outputs actuates the delivery mechanism to dispense medication to the patient.

In one embodiment, the physical testing apparatus measures body temperature, and the environment sensor measures room temperature. In this arrangement, the predetermined correlation is a body temperature that is above or below a predetermined level, while the sensed room temperature within prescribed conditions. Medication is dispensed to therapeutically treat the abnormal temperature condition, because the patient's physical condition cannot be attributed to the state of the patient's immediate environment.

In contrast, when the patient's abnormal temperature can be attributed to abnormal conditions in his/her immediate environment, medication is not dispensed.

In a preferred embodiment, the device further includes an environment control element for selectively changing the preselected environmental parameter. In this arrangement, the environment control element is actuated to change the sensed preselected environmental parameter in response to one of the outputs generated by the primary control element. Preferably, one of the outputs actuates the medication delivery means to treat the patient, while the other one of outputs actuates the environment control element to treat the environment.

In this arrangement, medication is not dispensed when the sensed room temperature is outside its prescribed limits. In this situation, corrective action is taken to return the room temperature to its prescribed limits.

Another aspect of the invention provides a patient monitoring and assistance device that includes physical testing apparatus usable by the patient for measuring a preselected physical parameter. The physical testing apparatus is operable in a first mode, during which it is retained within an associated housing away from access by the patient. The testing apparatus is also operable in a second mode during which the testing device is made available to the patient.

In this aspect of the invention, the device includes, as before described, an environment testing apparatus for measuring at least one preselected parameter in the patient's immediate environment. An input device is also provided for receiving and interpreting at least one prescribed command from the patient.

In this arrangement, a first control element shifts the operation of the physical testing apparatus from its first mode to its second mode in response to the receipt of interpretation of a prescribed command by the input device. A second control element compares the preselected physical parameter measured by the testing apparatus with the preselected environmental parameter measured by the environmental sensor. The second control element generates a first command signal when a predetermined correlation exists between the two parameters and generates a second command signal in the absence of the predetermined correlation. A first output is generated in response to the first command signal, and a second output, different from the first output, is generated in response to the second command signal.

In this arrangement, when a patient requests a test of his/her physical condition, the device also checks upon the condition of his/her immediate environment. The device correlates the two test results to obtain an accurate and meaningful indication of the present state of the patient's health.

Yet another aspect of the invention provides a patient monitoring and assistance device that includes a housing that carries a medication delivery mechanism. The medication delivery mechanism is operable in a first mode, during which it stores medication within the housing away from access by the patient. The medication delivery system is also operable in a second mode during which at least one dose of medication is made available to the patient.

In this aspect of the invention, the device includes environment testing apparatus for measuring at least one preselected parameter in the patient's immediate environment. An input device is also provided for receiving and interpreting prescribed commands from the patient.

In this aspect of the invention, upon the receipt and interpretation of a prescribed command by the input device that reflects a physical condition that could be related to the preselected environmental parameter, a first control element actuates the environment sensor to measure the preselected environmental parameter For example, a fever can be related to an elevated room temperature. A second control element determines whether the preselected environmental parameter measured by the environmental sensor is within prescribed limits. The second control element generates a first command signal when the sensed environmental parameter is within prescribed limits, and generates a second command signal when it is not. The medication delivery mechanism is actuated by the first output (indicating an abnormal physical condition not related to the physical environment), but not by the second output (indicating a possible link between the abnormal physical condition and the physical environment).

In a preferred embodiment, the device includes an environment control mechanism, as previously discussed, for changing the preselected environmental parameter. In this arrangement, the second output actuates the environment control mechanism to change the sensed preselected environmental parameter.

Also in a preferred embodiment, the input device receives and interprets at least one prescribed verbal command made by the patient.

Another aspect of the invention provides a medication delivery system that includes first and second medication dispensing mechanisms, each of which is independently actuated for administering medication to the patient. An environment testing apparatus is also provided to measure at least one preselected parameter in the patient's immediate environment. A control element actuates the first dispensing mechanism in response to a first administration criteria. The control element actuates the second dispensing mechanism in response to a second administration criteria different from the first criteria.

In accordance with this aspect of the invention, one of the first and second criteria includes, at least in part, a measurement based upon the preselected environmental parameter.

In a preferred embodiment, physical testing apparatus are also provided for the user to measure a preselected physical parameter. In this arrangement, one of the first and second criteria includes, at least in part, a measurement based upon the preselected environmental parameter and a measurement based upon the preselected physical parameter.

Other features and advantages of the invention will become apparent upon reviewing the following detailed description, drawings, and appended claims.

BRIEF DESCRIPTION OF THE DRAWINGS

FIG. 10 is an enlarged side view, partially broken away, of the medication delivery system shown in FIG. 3, tipped outwardly from the rear of the associated patient assist device for replenishment of medication;

FIG. 11 is an enlarged side view, partially broken away, of the medication delivery system shown in FIG. 3 in its operative position within the associated patient assist device; and FIGS. 12 to 15 are enlarged side views of the medication delivery system taken generally along line 12—12 in FIG. 3, showing the sequence of operation in dispensing medication in caplet form.

DESCRIPTION OF THE PREFERRED EMBODIMENTS

Figure 1:
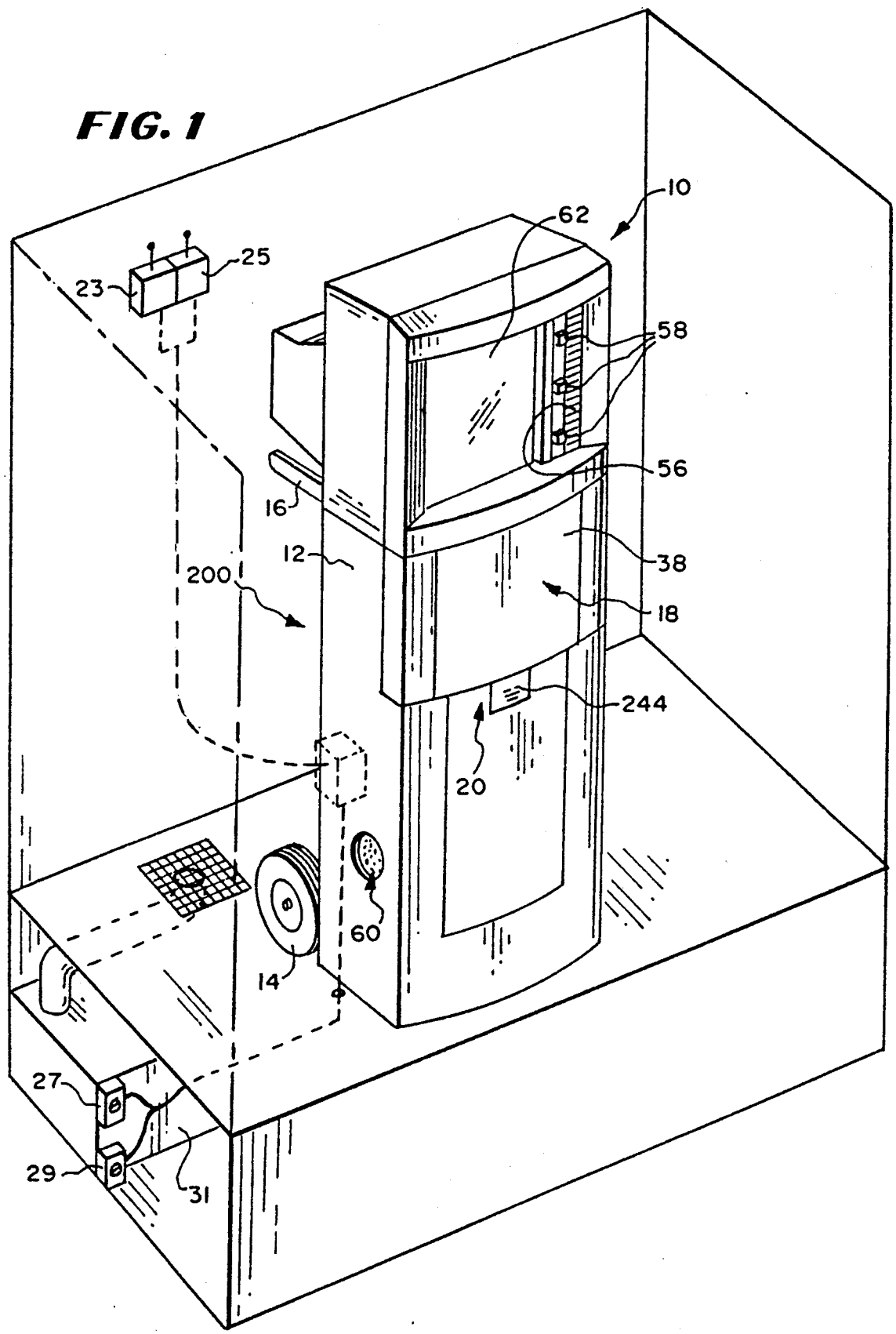
FIG. 1 is a front perspective view of a patient monitoring and assistance device having an enclosed system for delivering physical testing devices to the patient, an enclosed medication storage and dispensing system, each of which systems is shown in its closed position, and an environmental monitoring and control system that embodies the features of the invention.
Figure 2:
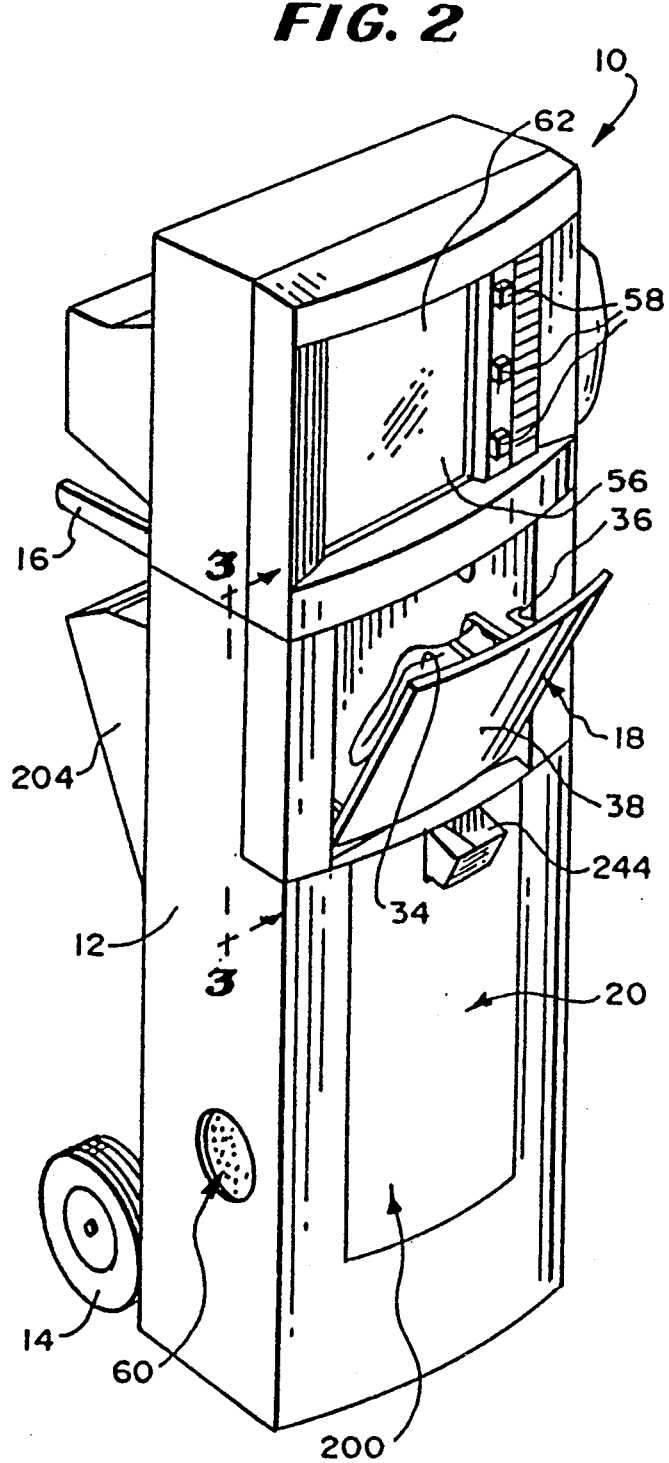
FIG. 2 is a front perspective view of the device shown in FIG. 1, with the testing device delivery system and medication delivery system each shown in its open position.

An interactive monitoring and assistance device 10 is shown in FIGS. 1 and 2. As will soon be described in greater detail, the device 10 performs as a self-contained, microprocessor-based caregiver who, in a friendly and supportive manner, monitors, manages and assists a patient in performing everyday health maintenance tasks. In carrying out its tasks, the device 10 monitors the patient's vital signs. In addition, the device 10 stores and administers medication. The device 10 also monitors and controls elements in the external environment that effect the patient's health and comfort. The device 10 is preferably linked to a central facility that provides round-the-clock supervision and response as required.

The device 10 includes a housing or cabinet 12 that, in a preferred design, stands about four feet tall. Preferably, the housing 12 is portable. For this purpose, the device 10 includes wheels 14 and a handle 16 for the patient, or another user, to guide the movement.

As shown in FIGS. 1 and 2, the device 10 houses a system 18 for storing and delivering one or more devices for testing the vital signals of a patient. The device 10 also houses a system 20 for storing and administering medication (see FIG. 3 also). The device 10 also contains a system 19 for monitoring and controlling the external environment of the patient. As will be described in greater detail later, the systems 18, 19, and 20 are interconnected.

Figure 4A:
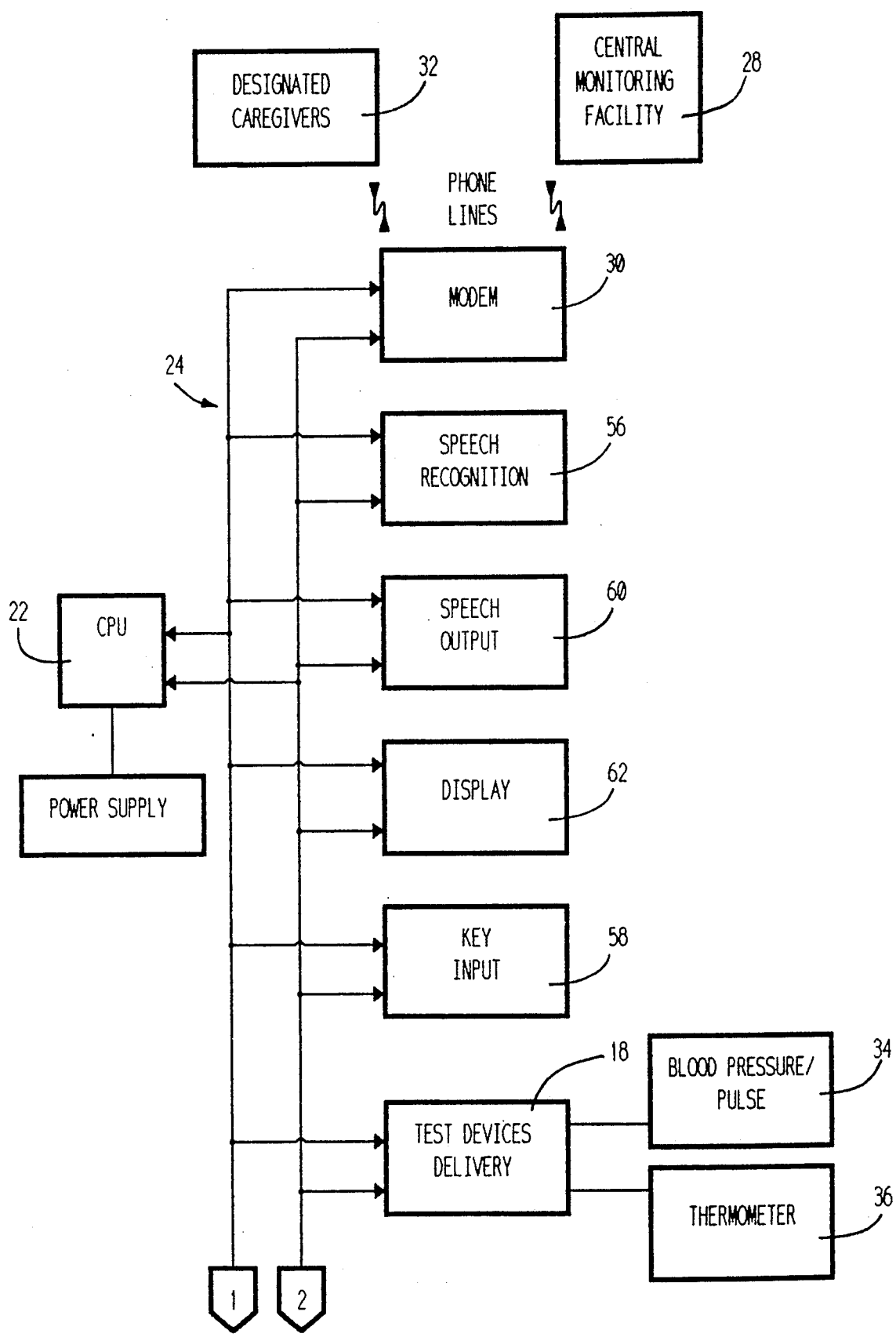
FIGS. 4a and 4b, said Figs. being collectively referred to hereinafter as FIG. 4, taken together are a schematic block diagram of the system that controls the operation of the patient assist device shown in FIG. 1.
Figure 4B:
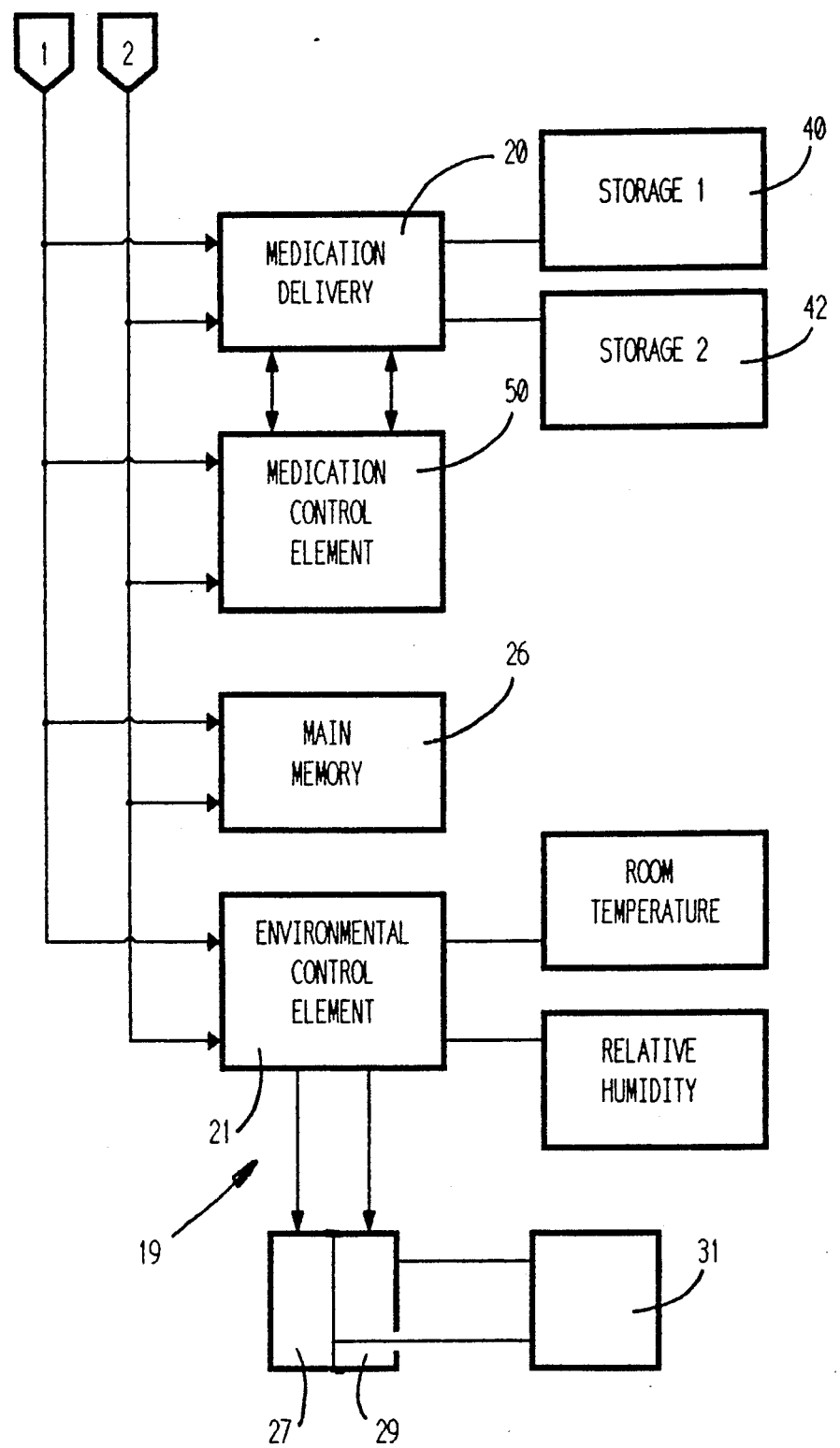

In the illustrated and preferred embodiment shown in FIG. 4, the device 10 houses a main microprocessor-based CPU 22 that coordinates and controls its operation. While various arrangements are possible, the CPU 22 preferably comprises an IBM PC compatible CPU board that accommodates multi-tasking sequences. Various input/output (I/0) devices communicate with the main CPU 22 through conventional data and address busses 24. The I/0 devices will be described in greater detail later. A mass storage device 26 for storing digital information also communicates with the main CPU 22 through the busses 24.

In use, as shown in FIG. 4, the device 10 is preferably linked with a central monitoring facility 28 by a modem 30 that communicates with the main CPU 22 through the busses 24. Health care professionals are present on a twenty-four hour basis at the central facility 28 to monitor the health of the patient based upon information collected and transmitted to them by the device 10.

The device 10 is also preferably linked via the modem 30 with selected individuals 32—typically close friends, family members, or other designated caregivers—who are automatically notified by the device 10 when certain health conditions exist or upon request by the patient or central facility 28.

As can be seen, the device 10 is a central part of an overall support system for the patient.

As shown in FIG. 2, the system 18 for monitoring the patient's vital signs includes two physical testing devices: a pressure cuff 34 for measuring blood pressure and pulse rate, and a thermometer 36 for measuring body temperature. Of course, other testing devices could be provided, depending upon the health condition of the patient and mode of treatment. As used herein, the term "physical test" broadly refers to tests of body functions (pulse, respiration, temperature, etc.) and tests of body fluids (blood, urine, saliva, etc.) by noninvasive and invasive techniques, including ultrasonic and radiographic methods.

As shown in FIG. 4, the testing devices 34 and 36 communicate with the main CPU 22 through the busses 24. The measurements taken are stored in the data storage device 26. These measurements are also periodically transmitted to the central monitoring facility 28 by the modem 30. The central facility 28 also preferably records received information in its own mass storage device for record keeping, retrieval and analysis.

Preferably, the testing devices 34 and 36 are housed in a movable compartment or drawer 38 within the housing 12. The drawer 38 is normally closed (as shown in FIG. 1), thereby retaining the testing devices 34 and 36 within the housing 12 away from access by the patient. The drawer 38 will open in response to an appropriate command signal received and interpreted by the main CPU 22. The opened position for the drawer 38 is shown in FIG. 2. The testing devices 34 and 36 are thereby made available for use by the patient. This particular operation will be described in greater detail later.

The environment monitoring system 19 includes a control means or element 21 that communicates with the main CPU 22 (see FIG. 4), either in the form of programmable random access memory (RAM) or as preprogrammed read only memory (ROM). According to its programming, the control element 21 is capable of receiving and evaluating at least one input that represents a physical measurement of a condition in the patient's immediate environmental condition that could effect the patient's health and comfort. In the illustrated embodiment (see FIG. 4), two input sensors 23 and 25 are linked to the control element 21. The input sensor 23 is a conventional sensor that monitors the room temperature. The other input sensor 25 is a conventional sensor that monitors the relative humidity of the room. These sensors 23 and 25 provide digital input for processing by the CPU 22. These sensors 23 and 25 can be linked to the control element 21 by wires or by remote radio telemetry.

Of course other input sensors could be used to monitor other environmental conditions, depending upon the health condition of the particular patient. For example, another input sensor (not shown) could monitor the quality of the air, detecting dust, pollen, and smoke.

The control element 21 also includes at least one output device that is capable of controlling or altering a condition in the patient's immediate environment. Preferably, the output device controls at least one environmental condition that is also sensed by one of the associated input sensors 23 and 25.

In the illustrated embodiment (see FIG. 4), two output control devices 27 and 29 are associated with the control element 21. The control device 27 is linked to the patient's heating and cooling system 31 by conventional means for controlling or altering the room temperature. The other control device 29, also linked to the patient's heating and cooling system 31 by conventional means, controls and alters the relative humidity of the room. These control devices 27 and 29 can be linked to the control element 21 by wires or by remote radio telemetry.

As can be seen in FIG. 4, the environmental control element 21 is linked via the busses 24 with the physical testing system 18, the medication delivery system 20, the central monitoring facility 28, as well as with all the other input and output systems (soon to be described) of the device 10. The environmental control element 21 is thereby an integral part of the overall monitoring and support system for the patient.

The medication delivery system 20 housed within the device 10 (see FIG. 3) is capable of storing and administering different types of medications having different administration criteria. The criteria can differ in terms of prescribed dosage amount, prescribed frequency of administration, degree of accessibility to the patient, or various combinations of the above.

As shown, the medication delivery system 20 includes at least two discrete storage compartments or cassettes (generally designated 40 and 42 in FIG. 3) within the housing 12. Each storage compartment 40 and 42 is separate and self-contained. Each compartment 40 and 42 is capable of independently storing at least one dose of a medication 44 within the housing 12 away from access by the user.

The medication delivery system 20 further includes independent delivery means or mechanisms associated with each storage compartment 40 and 42. In the illustrated arrangement (see FIGS. 3 and 5), a first delivery mechanism 46 is associated with the first storage compartment 40 for selectively delivering a medication dose from there to the patient. A second delivery mechanism 48 is likewise associated with the second storage compartment 42 for selectively delivering a medication dose from there to patient.

The number of individual delivery systems provided corresponds with the number of individual medication storage compartments. The number of storage compartments can, of course, vary. Only two storage compartments and their associated delivery systems will be discussed.

The first and second delivery mechanisms 46 and 48 operate independently and in response to different administration criteria. For this purpose (in particular, see FIG. 5), the medication delivery system 20 includes a control means or element 50 associated with the first and second delivery mechanisms 46 and 48. In the illustrated and preferred embodiment, the control element 50 communicates with the main CPU 22 (see FIG. 4, too), either in the form of programmable random access memory (RAM) or as preprogrammed read only memory (ROM).

According to its programming, the control element 50 is capable of receiving and differentiating between at least two different prescribed inputs. Upon the receipt and interpretation a first prescribed input or combination of inputs, the control element 50 will generate a control signal 52 that actuates the first delivery mechanism 46. Upon receipt of the second prescribed input or combination of inputs different from the first input, the control element 50 will generate a control signal 54 that actuates the second delivery mechanism 48. The control element 50 will not actuate the first delivery mechanism 46 in response to the second prescribed input.

Because the first and second control signals 52 and 54 are generated in response to different prescribed input criteria, the medications stored in the two storage compartments 40 and 42 can be selectively administered differently.

Figure 5:
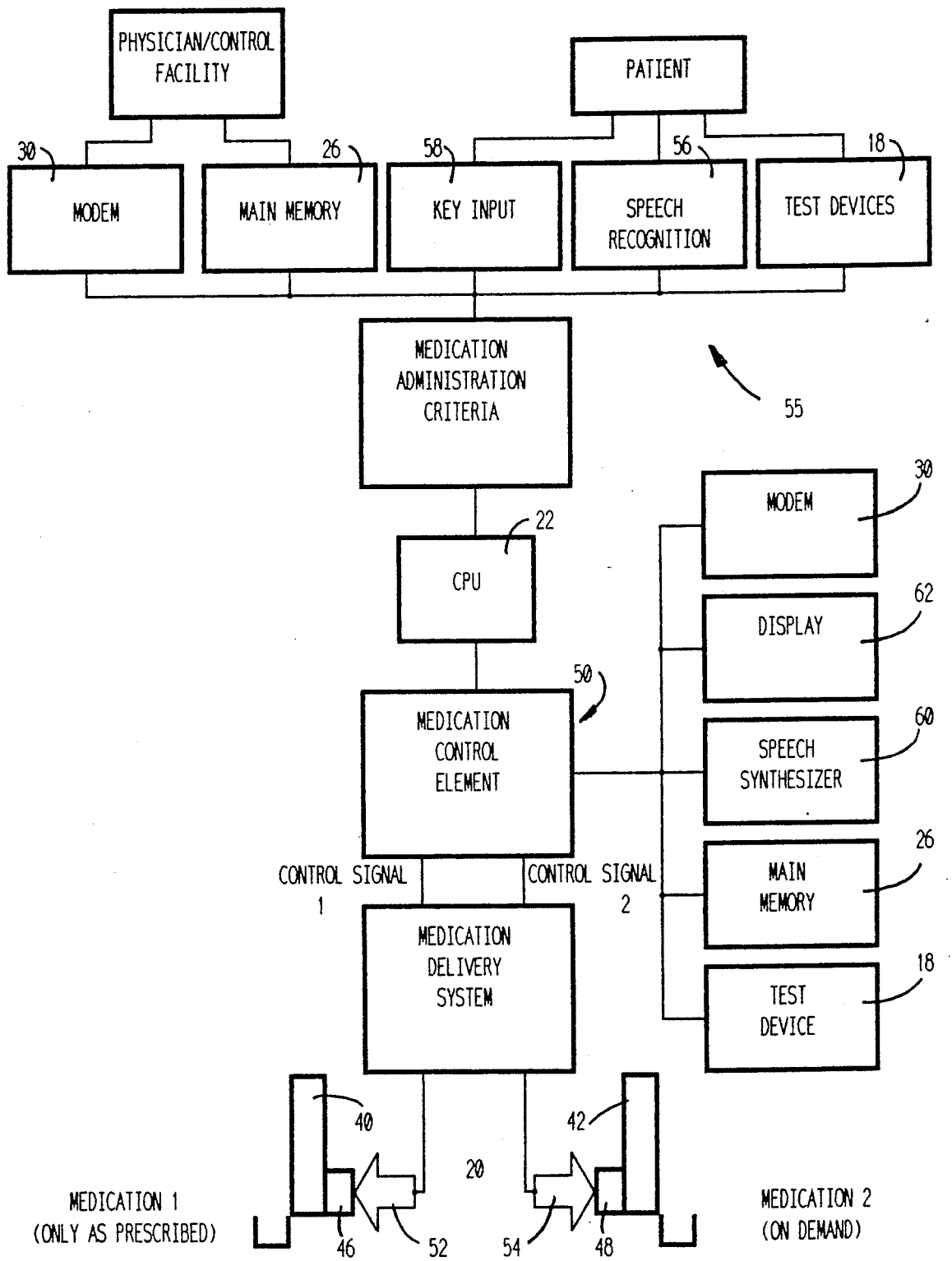
FIG. 5 is a schematic and partially diagrammatic block diagram of the elements of the system shown in FIG. 4 that control the operation of the medication delivery system.

As best shown in FIG. 5, the input criteria that generate the first and second control signals are derived from both external and internal devices 55 associated with the medication delivery system 20. These devices receive input from internal memory 26, the physician (or healthcare professional at the central monitoring facility 28), the individual patient, the physical testing devices 34 and 36, and the environmental sensors 23 and 25.

More particularly, the system 20 includes in internal memory 26 one or more prescribed schedules for administering medication. Here, the attending physician records the medication regime he or she has prescribed for the patient.

The system 20 also includes various external input devices for receiving and interpreting prescribed commands either from the patient or from the central monitoring facility 28. These external input devices communicate with the control element 50 through the main CPU 22 (see FIG. 4). The received commands can include one or more specified commands for administering medication "upon demand".

In the illustrated and preferred embodiment shown in FIGS. 4 and 5, the external input devices include a speech recognition system 56 for receiving and interpreting preselected verbal commands made by the patient (for example, by using a Texas Instruments Recognition and Speech Unit Model TI-2245186-001). The external input devices also include the modem 30 for receiving and interpreting preselected commands from the central facility 28.

In addition, the external input devices preferably include one or more input buttons or keys 58 located at a user-convenient place on the housing 12. The keys 58 allow the patient to manually enter the prescribed medication delivery commands, if desired. In the illustrated and preferred embodiment shown in FIGS. 1 and 2, only a select few input keys 58 for entering block (or macro-) commands are provided. This arrangement simplifies the patient's interface with the device 10. However, it should be appreciated that a full keyboard could also be included, depending upon the degree of sophistication and desires of the patient.

In the illustrated and preferred embodiment shown in FIGS. 4 and 5, the system also includes an external output device associated with the main CPU 22 for delivering messages or otherwise communicating with the patient. Preferably, the external output device includes a speech generation system 60 for generating audible messages to the user. The speech generation system 60 can take the form of either a conventional device that synthesizes speech or a conventional device that digitizes prerecorded speech.

In addition, the external output device also preferably includes a video monitor 62 on which the audible messages appear in written form (see FIGS. 1 and 2 also). In this arrangement, the video monitor 62 can also display in written form the preselected medication administration commands. In this way, the video monitor 62 serves to visually back up and confirm the verbal messages and commands being exchanged by the patient and the device 10, thereby minimizing the chance of misunderstandings or failures to communicate.

Due to these various input and output devices, the physical testing system 18, the environmental monitoring system 19, and the medication delivery system 20 all affirmatively interact with the patient, relying upon both spoken and written forms of communication with the patient.

System for Storing and Administering Scheduled Medication and On Demand Medication For example, the medication control element 50 as above described can store and selectively administer one category of medication that should be administered only according to a prescribed schedule and another category of medication that can be administered upon demand by the patient.

Figure 6A:
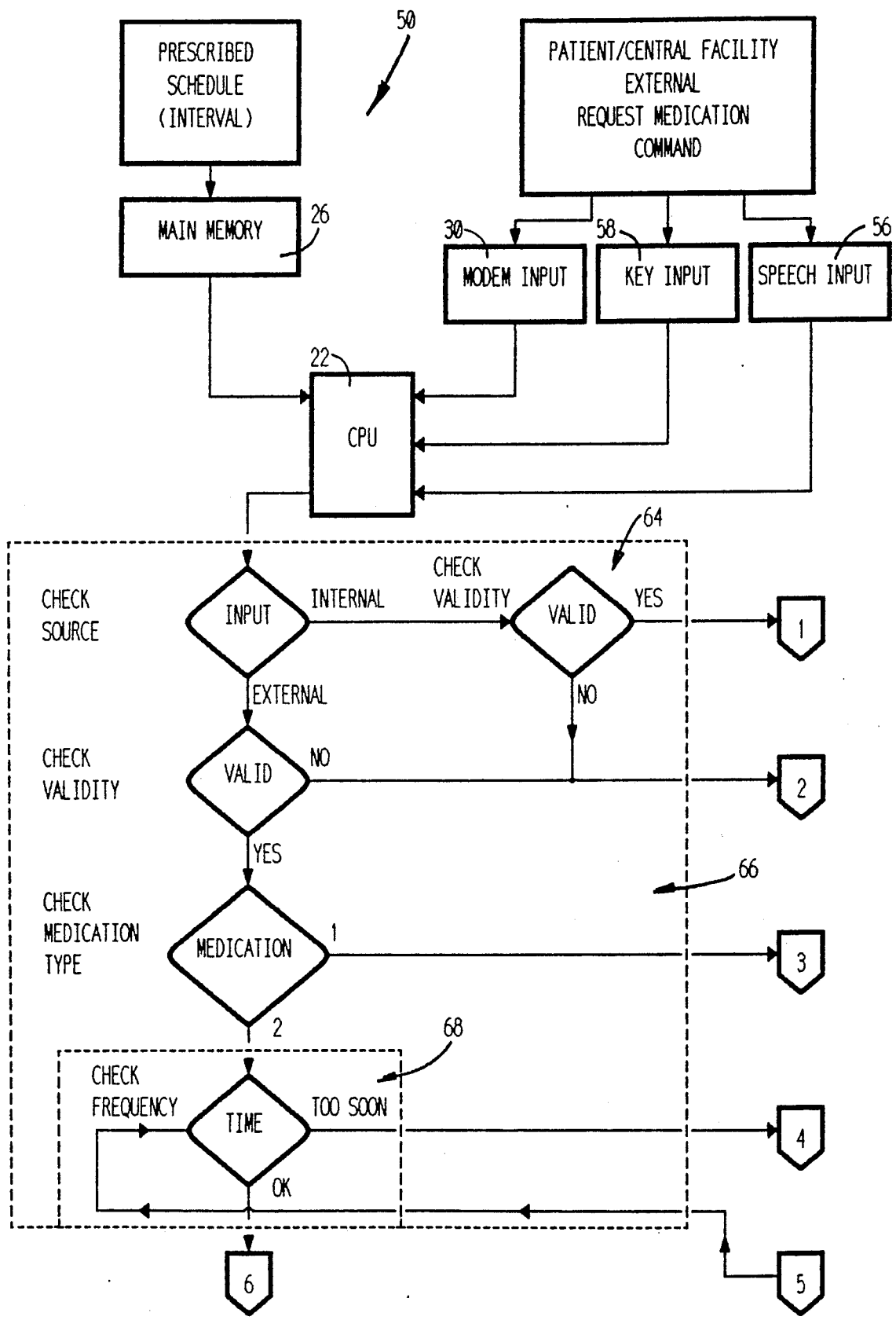
FIGS. 6a and 6b, said Figs. being collectively referred to hereinafter as FIG. 6.
Figure 6B:
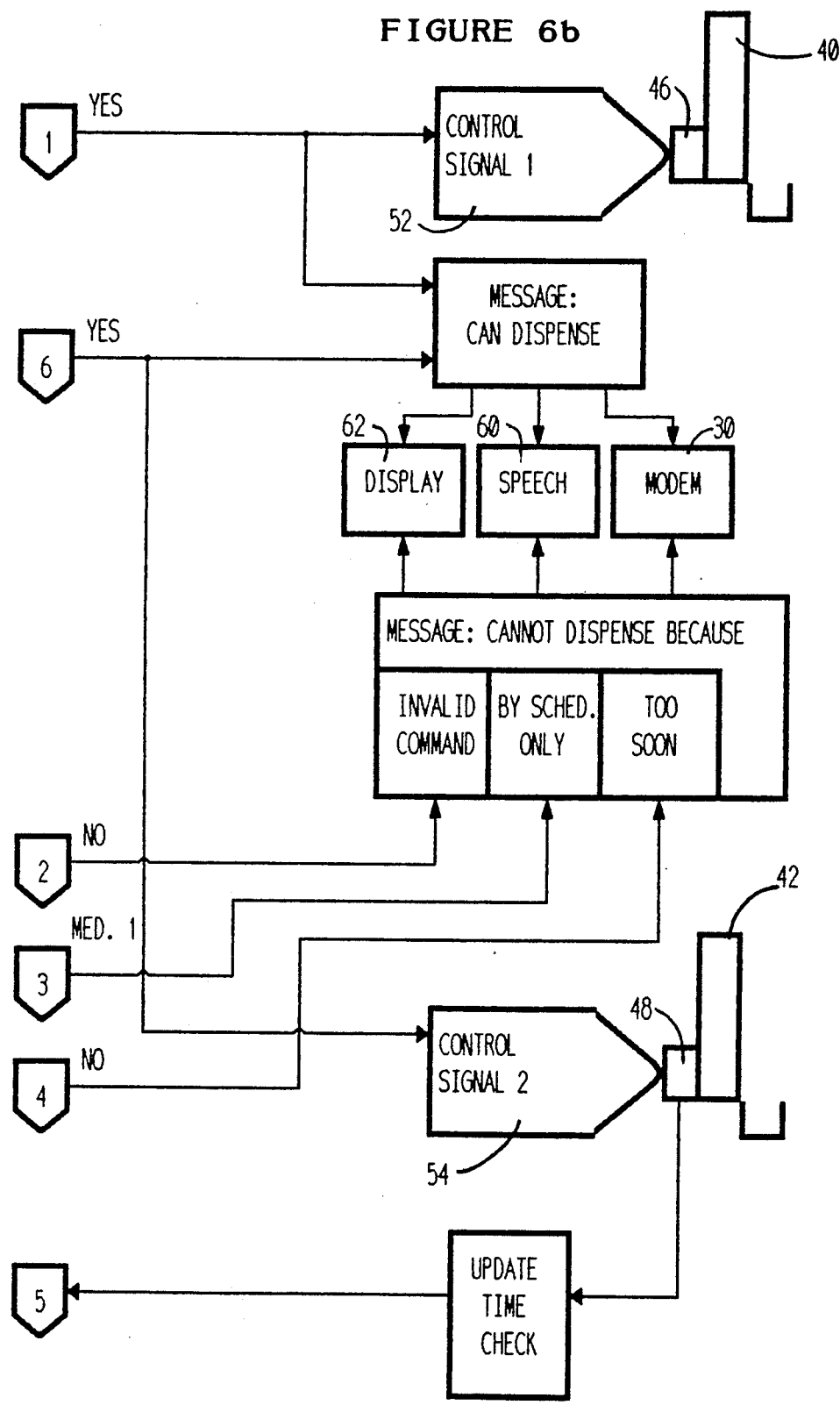

The control element 50 associated with this arrangement is shown diagrammatically in FIG. 6. The prescribed medication schedule is retained in the internal memory 26. The control element 50 includes a first operative sequence 64 that will generate the first control signal 52 upon receiving a valid administer medication command from an internal source (that is, a command generated internally based upon preprogrammed considerations). In the illustrated embodiment, the appropriate administer medication command is internally issued periodically by the CPU 22, based upon a continuous real time monitoring of the prescribed medication schedule stored in the internal memory 26.

Upon generation of the first control signal 52, medication retained in the first storage compartment 40, and only the first storage compartment 40, will be released to the patient.

Preferably, the first operative sequence 64 also generates a "Can Administer" message, using one or more of the output devices (the speech generator 60 and/or the display 62), advising the patient that the prescribed medication is being dispensed according to schedule.

The control element 50 also includes a second operative sequence 66 that, in association with the external input devices (modem 30/key input 58/speech recognition 56), receives and interprets one or more medication delivery commands received from an external source, such as the patient or the central facility 28. As shown in FIG. 6, the second operative sequence 66 conducts a validity check upon the command. The second operative sequence 66 also checks to determine what type or category of medication is being requested.

Upon receipt of a valid command or commands requesting the proper type of medication, the second operative sequence 66 generates the second control signal 54. The medication retained in the second storage compartment 42, but not the first storage compartment 40, is thereby released to the patient.

The second operative sequence 66 also preferably communicates an appropriate "Can Administer" message to the patient through one or more of the output devices 60/62. If the medication request originates from the patient, an advisory message may also be sent to the central facility 28 via the modem 30 at the time an "on demand" request is received and implemented.

If an invalid command is received, or if the patient requests a medication that can only be administered according to an internal command from the internal memory, an appropriate "Cannot Dispense" message is display and/or spoken using the output devices 60/62.

Preferably, whenever a decision is made to either dispense medication or withhold medication, the decision is recorded in internal memory 26 for record keeping purposes.

The first delivery mechanism 46 is thereby actuated in response to an internally generated command signal, but not in response to an externally generated command signal. The first category of medication can thus be safely retained within the first storage compartment 40 away from patient access, except as controlled by the control element 50 (via the first control signal 52). Strict compliance with the prescribed medication schedule is assured.

The second delivery mechanism 48 is actuated in response to the second control signal 54 based upon externally received commands. The second category of "on demand" medication can thus be safely retained in the second storage compartment 42 for administration externally controlled by the patient or the central facility 28 by issuing a proper external command.

In the illustrated and preferred embodiment shown in FIG. 6, the control element 50 also includes a third operative sequence 68 that maintains a real time record of "on demand" administrations of medication and the elapsed time period between them. The third operative sequence 68 includes timing means 70 for comparing the elapsed time between one actuation and the next subsequent actuation command to a prescribed fixed interval. The third operative sequence 68 will, based upon the output of the timing means 70, prevent the next subsequent actuation of the second delivery mechanism 48, despite the receipt of a valid medication command, when the elapsed time period is less than the prescribed period.

In the illustrated and preferred embodiment, the third operative sequence 68 also informs the patient through an appropriate "Cannot Administer" message via one or more of the output devices 60/62. In addition, an advisory message can also be transmitted to the central facility 28 via the modem 30. In this way, the system guards against mismedication or overuse of the "on demand" category of medication.

System for Storing and Administering Medication According to Present Health Parameters The control element 50 is also applicable for use when the different input criteria discriminate between one category of medication that can be administered only according to the schedule prescribed by the physician and another category of medication that can or should be administered when the then-existing health parameters of the patient dictate. The control element 50 of this arrangement is shown diagrammatically in FIG. 7. Components shared with the control elements 50 shown in FIG. 6 are given the same reference numerals.

In this arrangement, like the arrangements previously described, the prescribed schedule for administering medication is stored in the memory device 26. The first operative sequence 64 responds to this schedule in generating the first control signal 52, as previously described and shown in FIG. 6.

Figure 7A:
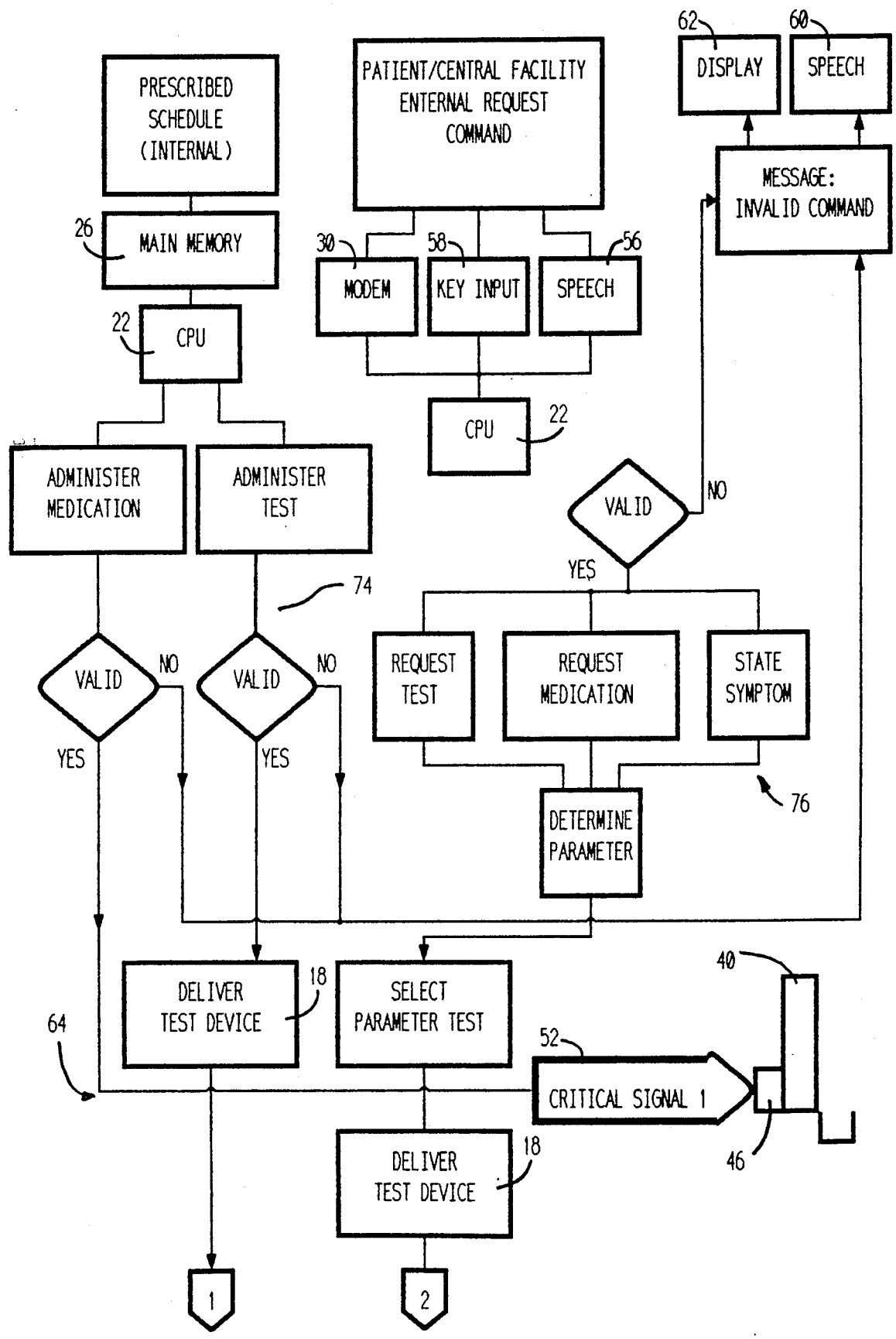
FIGS. 7a and 7b, said Figs. being collectively referred to hereinafter as FIG. 7 are schematic and partially diagrammatic flow charts of differing embodiments of the system for controlling the operation of the medication delivery system.
Figure 7B:
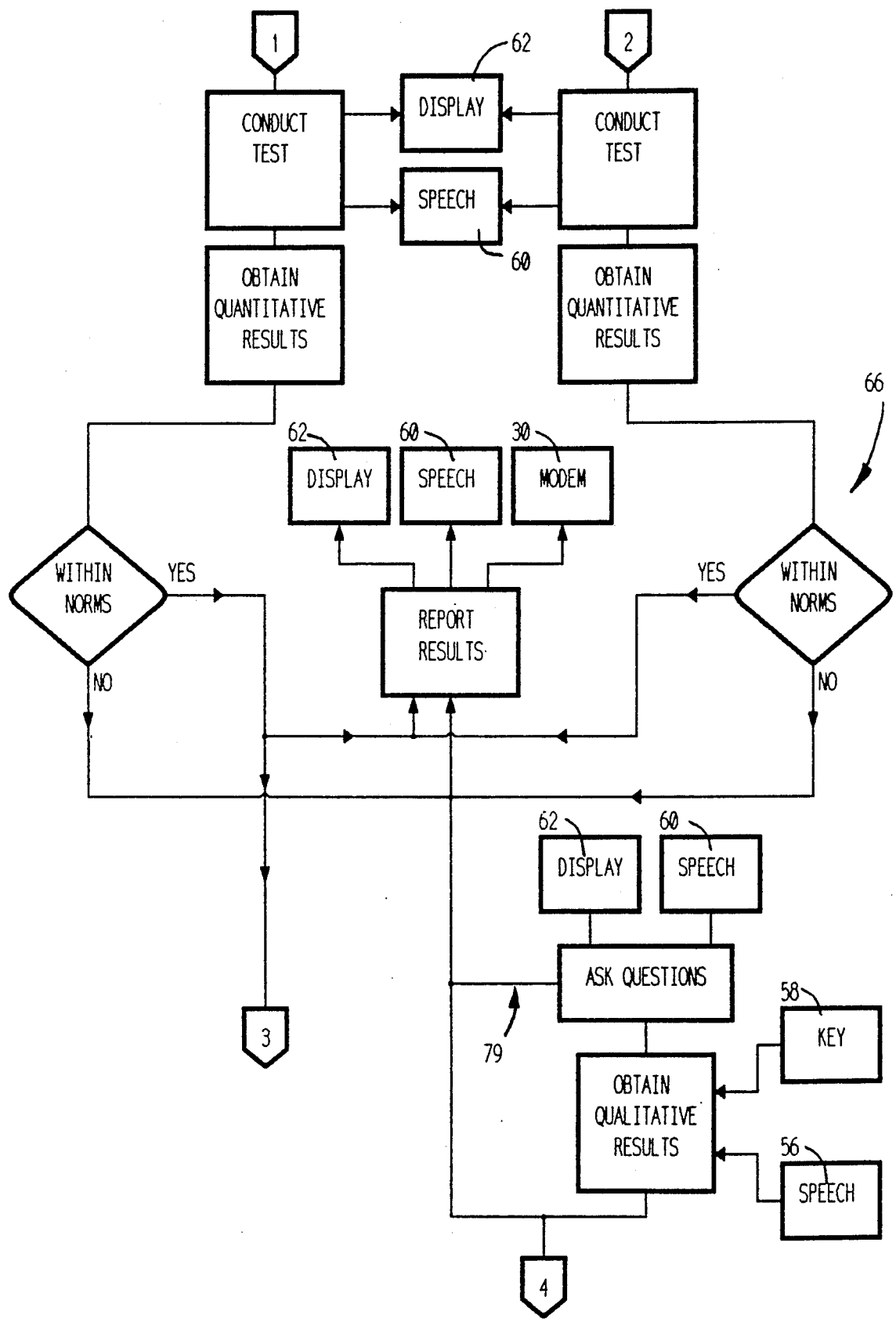
Figure 7C:
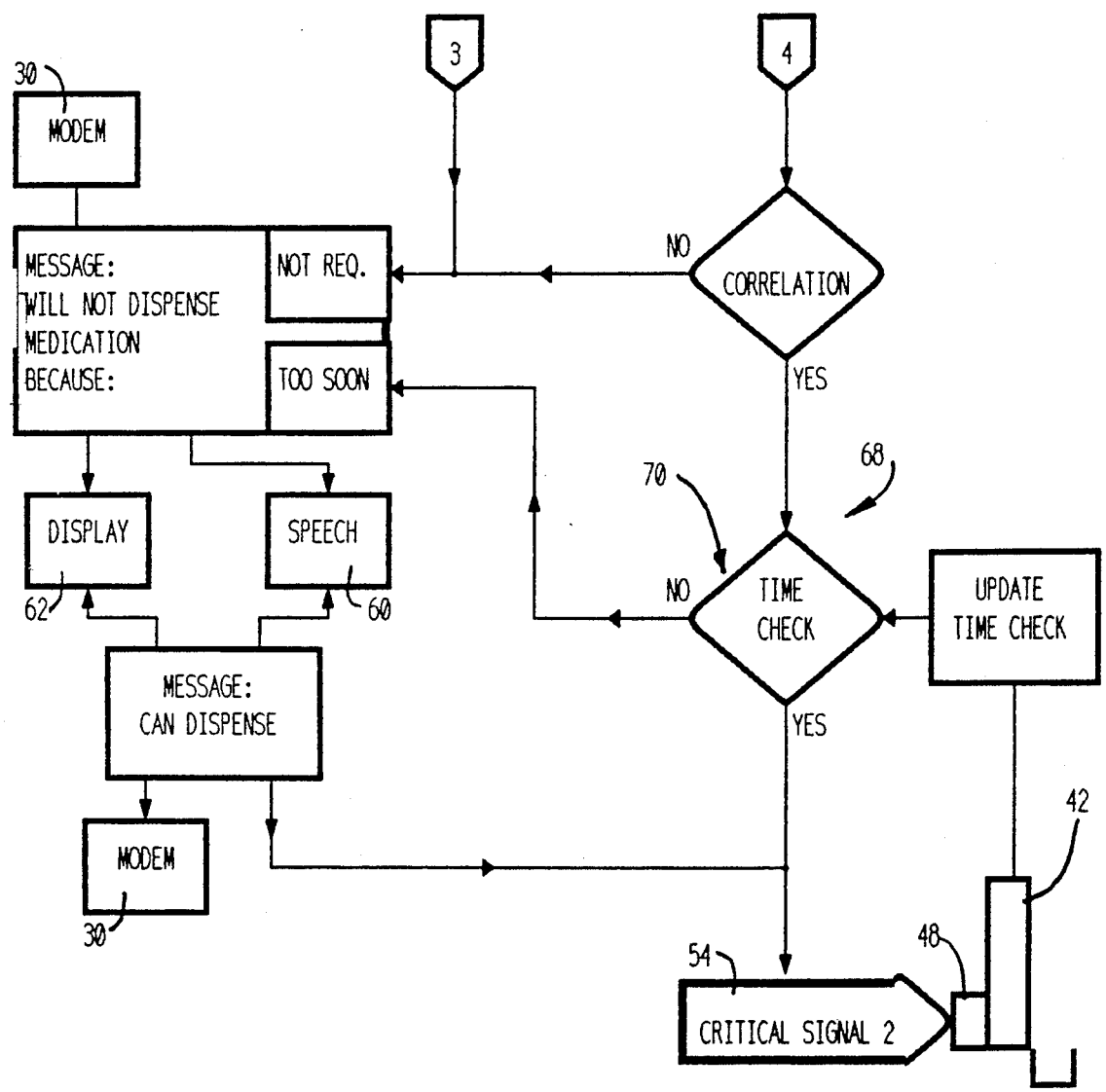

Unlike the other arrangements, however, the second operative sequence 66 shown in FIG. 7 receives and interprets information indicative of selected one or more health parameters of the patient. The second operative sequence 66 compares and correlates this information. If a prescribed correlation exists, indicating an abnormal health parameter that may respond to medication, the second operative sequence 66 generates the second control signal 54 to administer the appropriate medication through the second delivery mechanism 48.

In the illustrated and preferred arrangement shown in FIG. 7, the second operative sequence 66 collects its information from several different sources. One input comprises the quantitative measurements derived from the physical testing system 18. Another input comprises qualitative information received from the patient through the external input devices 56/58. Preferably, the second operative sequence 66 affirmatively interacts by prompting the patient, using the external output devices 60/62, to provide the qualitative and quantitative information necessary for the second operative sequence 66 to perform its required comparison and correlation sequence.

In the illustrated and preferred arrangement shown in FIG. 7, the second operative sequence 66 itself is prompted into action in one of two ways. In one sequence (path 74 in FIG. 7), an "Administer Test" signal is automatically generated according to a prescribed schedule stored in the main memory 26. This schedule carries out the attending physician's orders to periodically check the vital signs of the patient.

In another sequence (paths 76 in FIG. 7), the "Administer Test" signal is generated in response to an external command issued by the patient or by the central facility 28. For example, the patient can issue a prescribed command by voice (through input 56) or by key input 58 indicating a particular physical symptom ("I feel like I have a fever"), or a generalized feeling of discomfort ("I don't feel good"). Alternatively, the patient can issue a prescribed command requesting a specific test ("Check my temperature") or request medication ("Give me my pain pills").

The second operative sequence 66 preferably responds initially by requiring further information from the patient through a predetermined sequence of questions designed to isolate the particular physical parameter of concern. These requests are communicated through the output devices 60/62, and the responses are received through the input devices 56/58. Once the source of the physical problem is determined, the proper "Administer Test" signal is generated.

However generated, the "Administer Test" signal opens the drawer 38 (as shown in FIG. 2) to make the proper testing device(s) 34/36 available for use by the patient. The "Administer Test" signal also prompts the patient through the output communication devices 60/62 to conduct the desired test or tests.

In the illustrated embodiment (see FIGS. 10 and 11), the drawer 38 is biased toward an opened position by a control spring 76 (as shown in FIG. 10). A solenoid controlled locking mechanism 78 normally retains the drawer 38 in the closed and locked position (as shown in FIG. 11). An "Open" signal to the solenoid releases the locking mechanism 78 to allow the drawer 38 to open in response to the control spring 76. Other mechanisms can be used to accomplish this or a comparable function.

Referring back to FIG. 7, the quantitative test results obtained by the testing system 18 are compared to prescribed norms. If the test results are within prescribed norms, the second operative sequence 66 issues an appropriate "Will Not Dispense Medication" message through the appropriate output devices 60/62. The normal test results are reported to the patient (via output devices 60/62) and, preferably, to the central facility 28 (via the modem 30) as well.

However, if the quantitative test results are not within prescribed norms, the second operative sequence 66 of the control element 50 proceeds with its further evaluation, taking into account still additional qualitative and quantitative considerations.

For example, should the patient complain of a fever, and the quantitative test results establish an above average temperature, the second operative sequence 66 may additionally prompt the patient, using the external output devices, with a series of questions relating to recent activities, such as exercise or eating, that may effect body temperature. The patient's responses are received and interpreted through the external input devices 56/58.

The second operative sequence 66 of the control element 50 compares and correlates this qualitative and quantitative information in accordance with preprogrammed diagnostic routines. If a correlation exists indicating that the patient has a temperature that is unrelated to recent activities, the second operative sequence 66 generates the second control signal 54 required to activate the second delivery mechanism 48 where the prescribed temperature reducing medication is stored.

In this situation, the second operative sequence 66 also preferable communicates with the patient with an appropriate "Can Dispense Medication" message (via the display 62 and with output speech device 60) and provides an advisory message to the central facility 28 using the modem 30.

In the preferred embodiment, the timing means 70 of the third operative sequence 68 is provided, along with the appropriate advisory message, to assure that symptom-specific medication is not administered too often.

If a correlation does not exist, or if a repeat administration is sought within a given time period, the patient is so informed by an appropriate "Will Not Administer Medication" message, and no medication is administered. However, an advisory message may nevertheless be transmitted to the central facility 28 or to a designated caregiver 32 using the modem 30.

Figure 3:
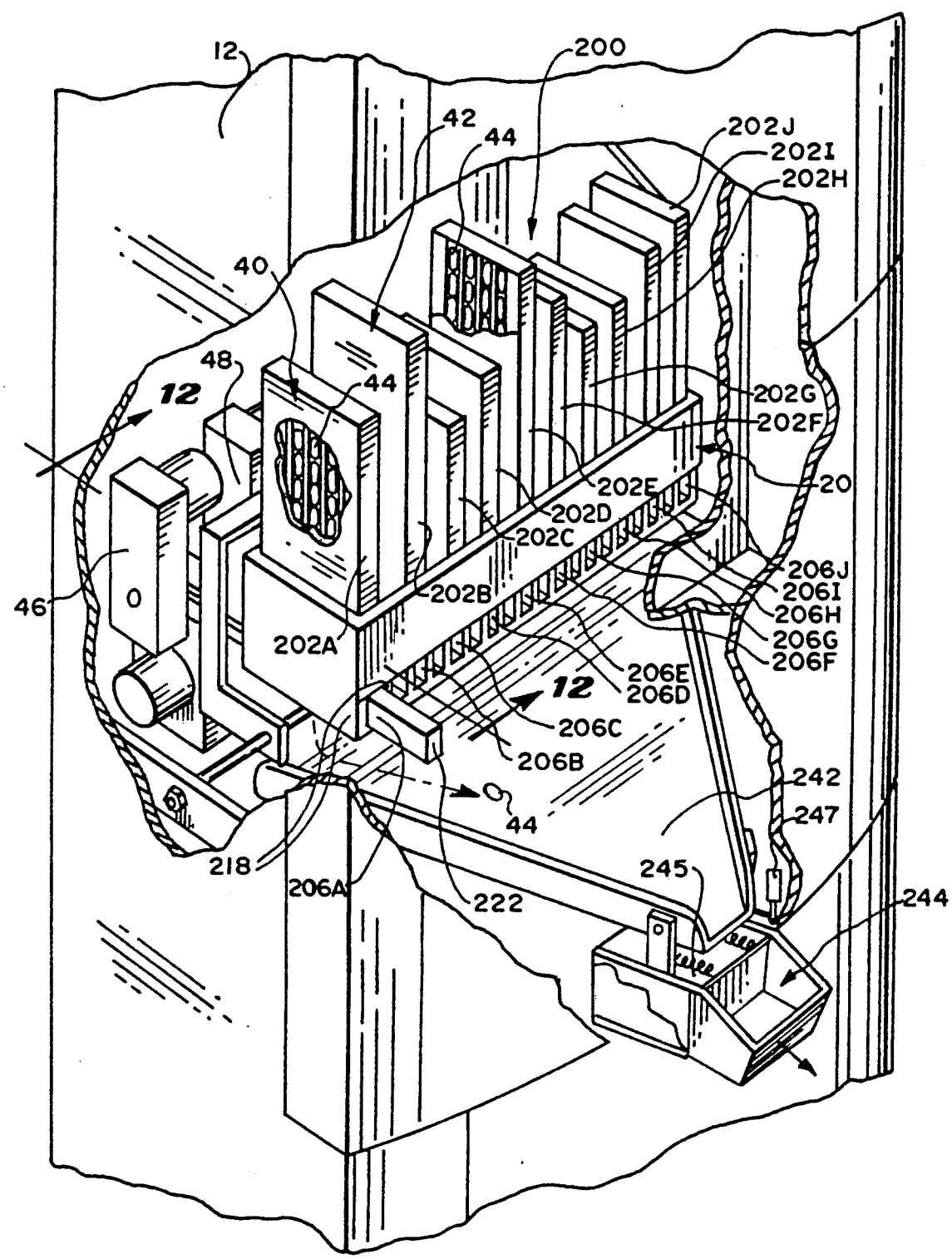
FIG. 3 is an enlarged perspective view, with portions broken away, of the interior of the device shown in FIG. 2, showing the enclosed medication storage and dispensing system.

As shown in FIG. 3, the medication delivery system can separately store several different types of medication to treat different physical symptoms, such as high temperature, indigestion, or body pains. The control element 50 can receive and correlate the qualitative and quantitative information, and, upon arriving at a prescribed correlation, generate the specific control signal to administer the appropriate type of medication, depending upon the symptom encountered.

System for Controlling the Immediate Physical Environment of the Patient

The environmental control system 19 above described can affirmatively interact with the patient as well as with the physical testing and medication administration systems 18 and 20 in various beneficial ways.

Figure 8A:
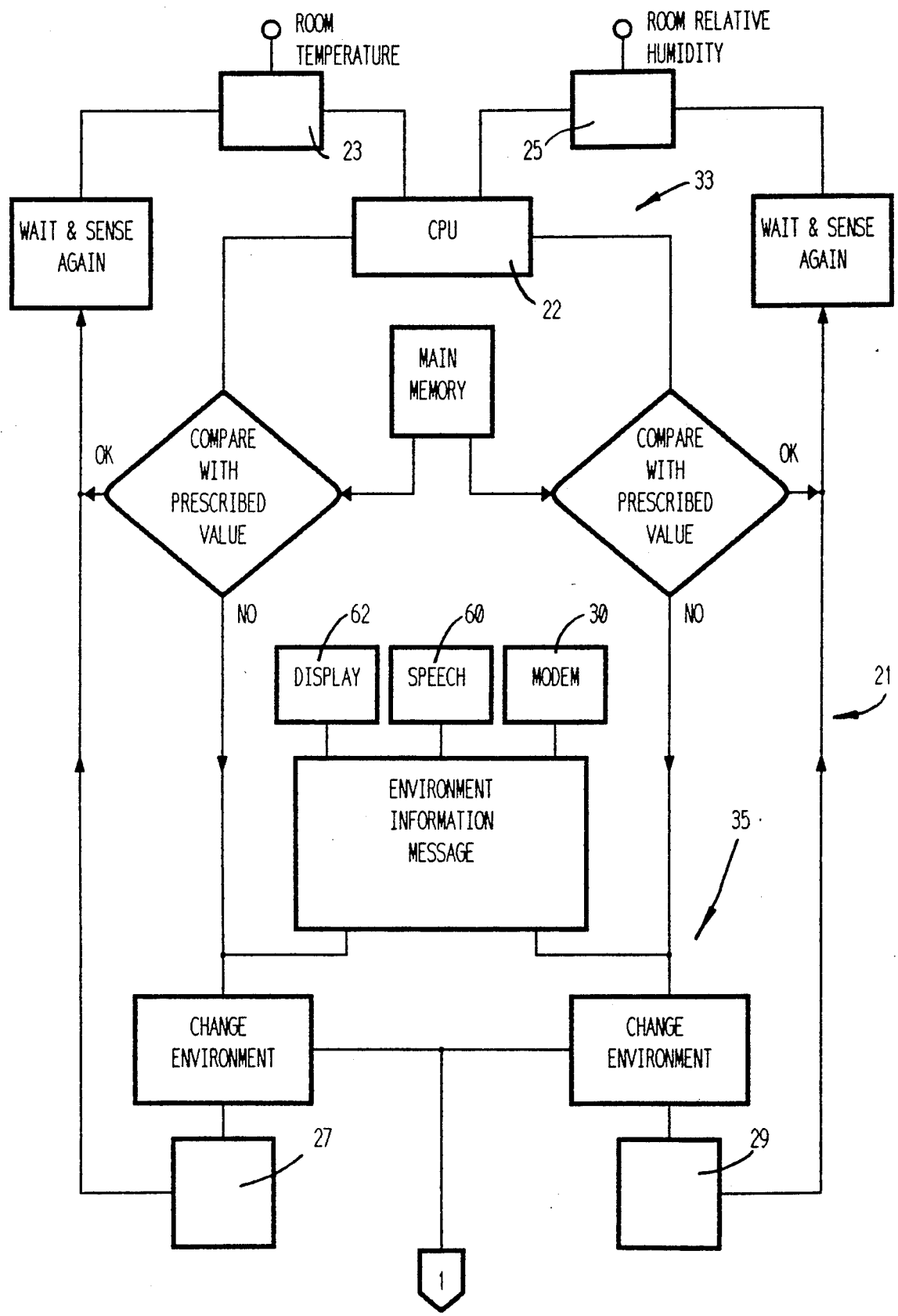
FIGS. 8a and 8b, said Figs. being collectively referred to hereinafter as FIG. 8, taken together are a schematic and partially diagrammatic flow chart of the control element associated with the environmental monitoring system that embodies the features of the invention.
Figure 8B:
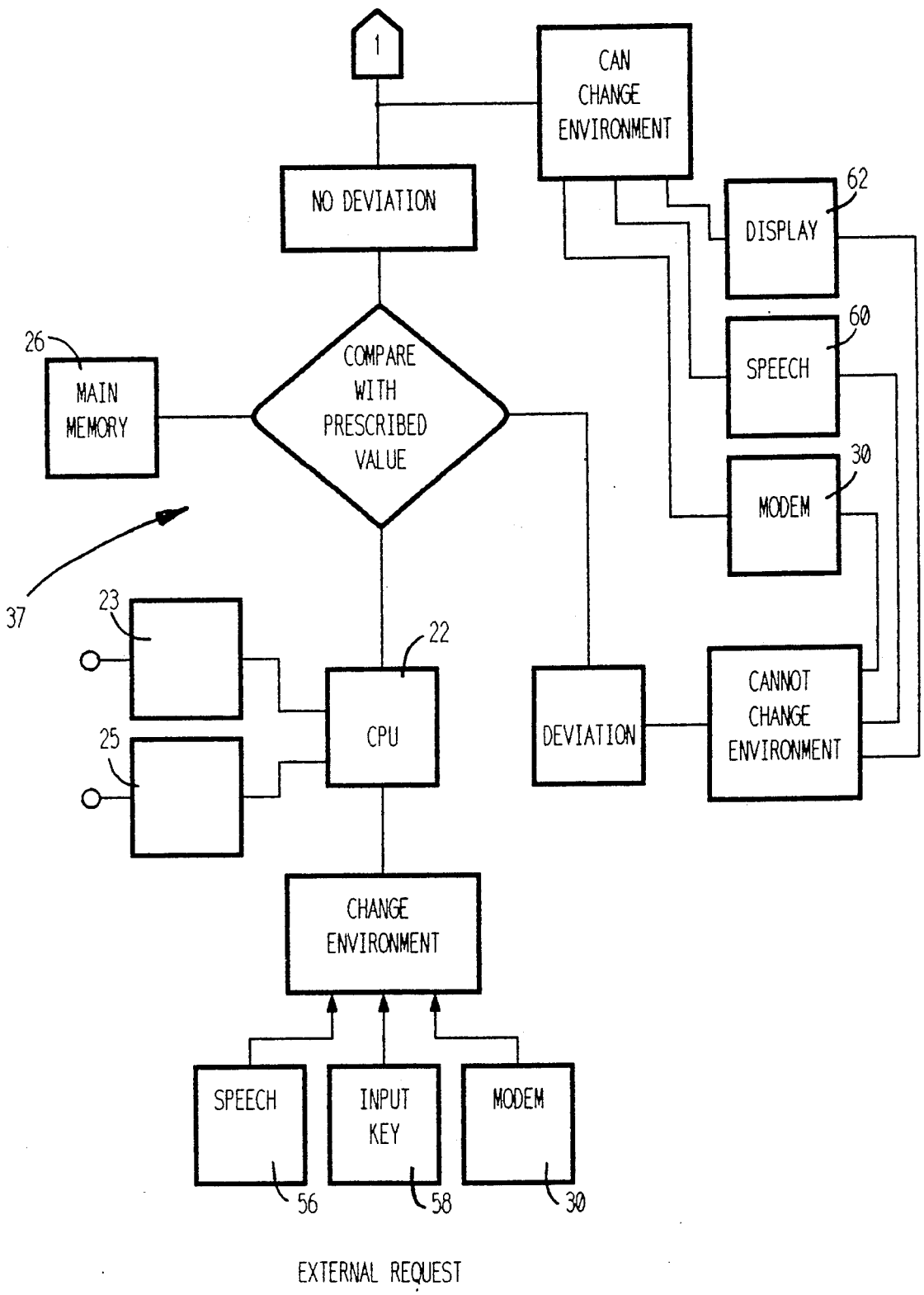

As shown in FIG. 8, the environmental control element 21 can periodically monitor the temperature and relative humidity values of the room (via the sensors 23 and 25). The control element 21 includes a first operative sequence 33 which compares the sensed environmental values to prescribed values or ranges of values contained in main memory 26. These prescribed conditions can be established by the attending healthcare professional or by the associated caregiver 32. For example, the physician may require a room temperature in the range of 68 to 72 degrees Fahrenheit. The physician may also require a relative humidity index of between 40 and 60%.

If the sensed conditions do not meet the prescribed conditions, the sequence 33 generates an appropriate "Environment Information" message to the patient via the output devices 60 and 62. An appropriate "Environment Information" message can also be transmitted to the central monitoring facility 28 or the associated caregiver 32 via the modem 30.

The "Environment Information" message informs the patient that conditions in his/her immediate environment need adjustment. The message can request the patient to take the steps necessary to correct the sensed variance by, for example, manually adjusting the thermostat of the heating and cooling system 31.

In the illustrated and preferred embodiment (see FIG. 8), the control element 21 includes a second operative sequence 35 that issues an internal "Change Environment" command that automatically corrects the sensed variance using the output control devices 27 and/or 29.

In the illustrated and preferred embodiment (see FIG. 8), the control element 21 further includes a third operative sequence 37 that receives and interprets an external "Change Environment" command from the patient (via the input devices 56/62/58) or from the central monitoring facility 28 or associated caregiver 32 (via the modem 30). Upon receipt of a "Change Environment" command, this operative sequence 37 first senses the existing environmental conditions (via the sensors 23 and 25) and compares them to the prescribed conditions in main memory 26 to determine whether the prescribed environmental conditions will accommodate the requested change. If the requested change will cause an unauthorized deviation, the sequence 37 generates an appropriate "Cannot Change Environment" message (via the output devices 60 and 62 or modem 30, depending upon the source of the request). However, if the requested change will not cause an unauthorized deviation from the prescribed conditions, the sequence 37 generates an appropriate "Can Change Environment" message, using the same output devices 60/62 or modem 30, and will issue the appropriate internal "Change Environment" command.

System for Administering Medication According to Present Health Parameters and Immediate Physical Environment The control element 21 is also applicable to establish different input criteria controlling the administration of physical tests and/or medication to the patient. The control element 21 of this arrangement is shown diagrammatically in FIG. 9. Components shared with the control element 50 shown in FIG. 7 are given the same reference numerals.

In this arrangement, it is contemplated that, like the arrangement previously described in FIG. 7, a prescribed schedule for administering medication is stored in the memory device 26. The first operative sequence 64 of the medication control element 50 responds to this schedule in generating the first control signal 52, as previously described and shown in FIG. 7, to administer medication through the first delivery mechanism 46. This particular delivery sequence is shown in FIG. 7, and is not duplicated in FIG. 9.

Figure 9A:
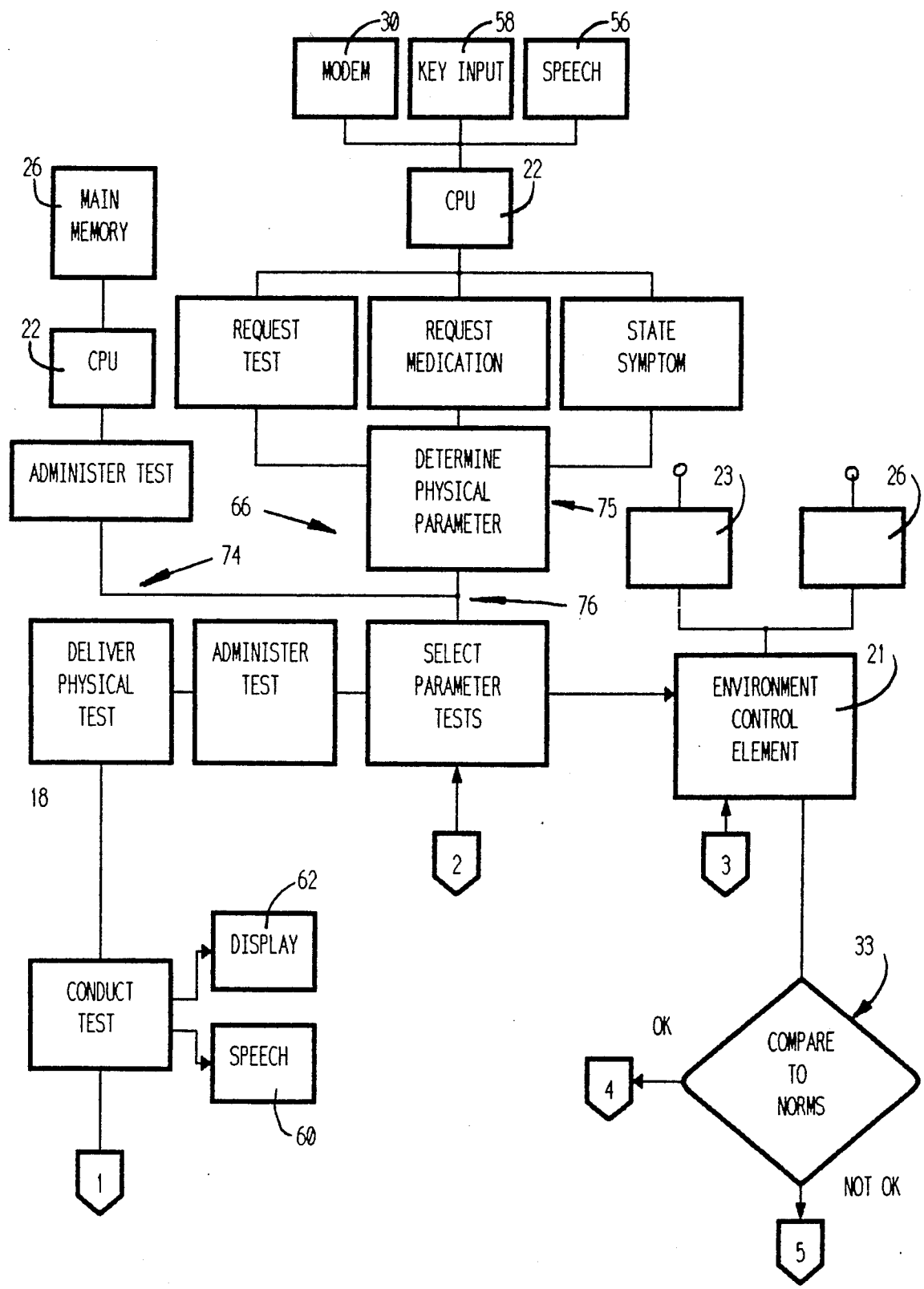
FIGS. 9a and 9b, said Figs. being collectively referred to as FIG. 9 taken together are a schematic and partially diagrammatic flow chart of a physical testing and medication dispensing system that incorporates the control element shown in FIG. 8.
Figure 9B:
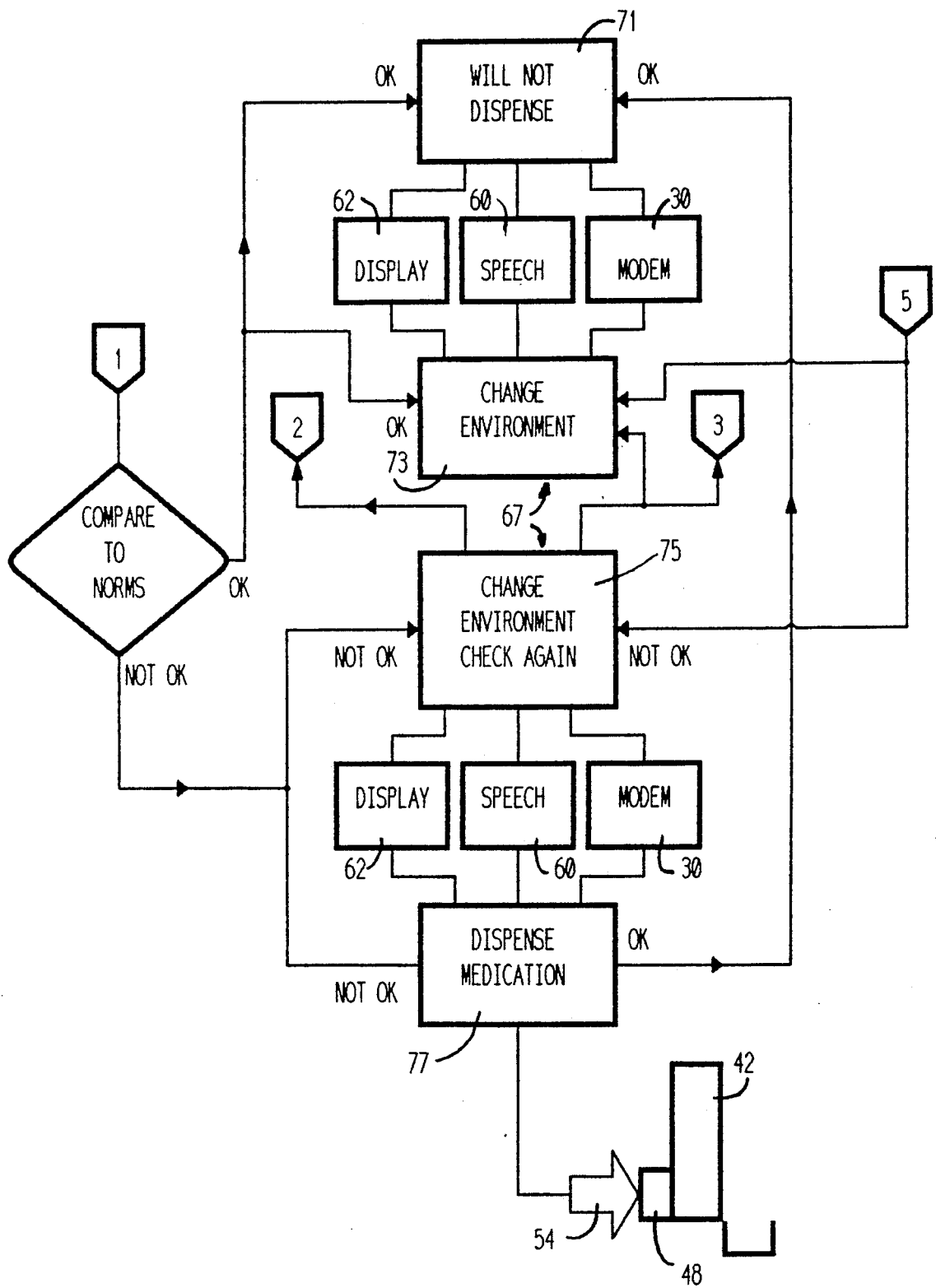

Also like the arrangement shown in FIG. 7, the second operative sequence 66 of the medication control element 50 receives and interprets information indicative of selected one or more physical health parameters of the patient. Medication is dispensed through the second delivery mechanism 48 through this sequence 66. In FIG. 9, unlike the arrangement shown in FIG. 7, the second operative sequence 66 also receives and interprets information from the control element 21 reflecting the condition (temperature and relative humidity) of the patient's immediate environment. Therefore, in FIG. 9, the second operative sequence 66 compares and correlates information indicative of both the internal physical health of the patient and the immediate external environment of the patient.

If a prescribed correlation exists, indicating an abnormal health parameter that (1) may respond to medication and (2) is not attributable a current environmental condition, the second operative sequence 66 generates the second control signal 54 to administer the appropriate medication through the second delivery mechanism 48.

In the illustrated and preferred arrangement shown in FIG. 9, the second operative sequence 66 is prompted into action in one of two ways. In one sequence (path 74 in FIG. 9), an "Administer Test" signal is automatically generated according to a prescribed schedule stored in the main memory 26. This schedule carries out the attending physician's orders to periodically check the vital signs of the patient.

In another sequence (generally shown as path 76 in FIG. 9), the "Administer Test" signal is generated in response to an external command issued by the patient or by the central facility 28. For example, the patient can issue a prescribed command by voice (through input 56) or by key input 58 indicating a particular physical symptom ("I feel like I have a fever"), or a generalized feeling of discomfort ("I don't feel good"). Alternatively, the patient can issue a prescribed command requesting a specific test ("Check my temperature") or request specific medication ("Give me my pain pills").

The second operative sequence 66 preferably responds initially by requiring further information from the patient through a predetermined sequence 75 of questions designed to isolate the particular physical parameter of concern to the patient. While not specifically shown in FIG. 9, these requests are communicated through the output devices 60/62, and the responses are received through the input devices 56/58. Once the source of the physical problem is determined, the proper physical parameter test is selected and the corresponding "Administer Test" signal is generated.

However generated, the "Administer Test" signal opens the drawer 38 (as shown in FIG. 2) to make the proper testing device(s) 34/36 available for use by the patient. The "Administer Test" signal also prompts the patient through the output communication devices 60/62 to conduct the desired test or tests.

In the illustrated embodiment (see FIGS. 10 and 11), the drawer 38 is biased toward an opened position by a control spring 76 (as shown in FIG. 10). A solenoid controlled locking mechanism 78 normally retains the drawer 38 in the closed and locked position (as shown in FIG. 11). An "Open" signal to the solenoid releases the locking mechanism 78 to allow the drawer 38 to open in response to the control spring 76. Other mechanisms can be used to accomplish this or a comparable function.

Once the proper physical parameter is isolated, the sequence 66 also selects the closest associated environmental parameter(s) that is being monitored. For example, if the patient complains of fever, the room temperature parameter is selected. The control element 21 is actuated to measure the present room temperature (through sensor 23). The control element 21 determines through its operative sequence 33 (shown in FIG. 8) whether the selected environmental parameter is within the prescribed value. This output is transmitted to a comparator 67 in the operative sequence 66.

At the same time, the quantitative results of the physical parameter tests are compared to the established norms. This output is also transmitted to the comparator 67.

The comparator 67 determines whether a correlation exists between the physical symptom complained about and a condition in the patient's immediate environment.

If the physical test results are within prescribed norms, and the environmental test results are also within prescribed values, the second operative sequence 66 issues a command 71 that results in an appropriate "Will Not Dispense Medication" message through the appropriate output devices 60/62 (as shown in more detail in FIG. 7). The normal physical and environmental test results are reported to the patient (via output devices 60/62) and, preferably, to the central facility 28 (via the modem 30) as well (as also shown in more detail in FIG. 7).

If the physical tests results are within prescribed norms, but the environmental tests results are not (indicating the need to alter the environment), the sequence 66 issues a different command 73 that results in an appropriate "Change Environment" message through sequence 33 of the control element 21 (as shown in FIG. 8). As shown in more detail in FIG. 7, an appropriate "Will Not Dispense Medication" message is issued through the appropriate output devices 60/62. The normal physical and abnormal environmental test results are also reported to the patient (via output devices 60/62) and, preferably, to the central facility 28 (via the modem 30) as well (see FIG. 7).

If both the physical tests results and the environmental test results are not within prescribed norms (indicating a possible correlation between physical and environmental conditions), the sequence 66 issues a command 75 that also results in an appropriate "Change Environment" message through sequence 33 of the control element 21 (see FIG. 8 also). The command 75 will also wait for the environmental change to take effect and repeat the testing sequence, once the environmental conditions return to normal. As shown in more detail in FIG. 7, an appropriate "Will Not Dispense Medication" message is issued through the appropriate output devices 60/62. The abnormal physical and abnormal environmental test results are reported to the patient (via output devices 60/62) and, preferably, to the central facility 28 (via the modem 30) as well (see FIG. 7).

If the quantitative physical test results are not within prescribed norms, while the environmental tests results are (indicating no correlation between physical and environmental conditions), the sequence 66 issues another different command 77. As shown in FIG. 9, this command 77 results with the issuance of the second control signal 54 to dispense medication through the second delivery mechanism 48 where the prescribed temperature reducing medication is stored.

In an alternate arrangement, shown in path 79 in FIG. 7, the command 75 issued when there is no correlation between the physical and environmental test results can cause the sequence 66 to proceed with further evaluation of the patient's physical condition, taking into account still additional qualitative and quantitative considerations, as previously described.

In either this situation or the situation shown in FIG. 9, the second operative sequence 66 also preferable communicates with the patient with an appropriate "Can Dispense Medication" message (via the display 62 and with output speech device 60) and provides an advisory message to the central facility 28 using the modem 30 (see FIG. 7).

The timing means 70 of the third operative sequence 68 (shown in FIG. 7) may also be provided, along with the appropriate advisory message, to assure that symptom-specific medication is not administered too often.

As shown in FIG. 3, the medication delivery system can separately store several different types of medication to treat different physical symptoms, such as high temperature, sore throat, chills or body pains. The control element 50 can receive and correlate the qualitative and quantitative information, and, upon arriving at a prescribed correlation, generate the specific control signal to administer the appropriate type of medication, depending upon the symptom encountered.

It should be appreciated that environmental conditions can be correlated in different ways or combination of ways to the administration of medication and/or the administration of physical tests.

For example, the sequence 66 can test environmental conditions prior to or after conducting a physical test and perform the same correlation shown in FIG. 9, except in a different order. In one such alternate arrangement, if a physical test is requested, the sequence 66 can first test the closest associated environmental parameter to determine whether it is within established norms. If it is, the sequence 66 can then proceed to conduct the physical test. If the environmental test is not within the norms, the sequence can proceed to change the environment and bring it into normal conditions before any conducting physical tests.

In another alternative arrangement, the sequence 66 can test environmental conditions only after a physical test demonstrates an abnormal physical condition.

Regardless of the timing of the environmental testing, the same underlying beneficial aspects of the invention are being applied.

A Representative Medication Dispenser

The specific configuration of the interactive medication delivery system 20 as above described can vary according to the form in which the medication is administered. For example, one or more types of medication can be administered in predetermined dosages in sealed packets or "blister packs". Alternatively, or in combination, single dosages of a medication can be administered in a pill or caplet form, either in unsealed, "loose" form or on sealed rolls.

Attention is directed to FIGS. 1 to 3 and 10 to 15, where a representative system 200 for storing and delivering individual pills or caplets is shown.

The system 200, is carried within the confines of the patient monitoring and assistance device 10 (see FIGS. 1 to 3). The system 200 includes discrete medication storage compartments 202 A through J (see FIG. 3). The storage compartments 202 are each capable of separately storing medication in pill or caplet form.

In the illustrated embodiment shown in FIG. 3, there are ten storage compartments 202 located within an enclosed housing. Of course, the number of individual compartments can vary according to the needs of the patient. Each compartment 202 is capable of holding a number of individual pills/caplets (designated by reference numeral 44 in FIG. 3). The number of pills/caplets carried within each compartment 202 is determined by the physician according to the demands of the particular medication regime and how often the medication is to be replenished. Typically, a two week supply of medication can be contained within each compartment 202.

As shown in FIG. 3, the pills/caplets 44 are arranged side-by-side in a plurality of vertically stacked columns 208 within each compartment 202. As shown in FIG. 3, the compartments 202 preferably differ in overall vertical height and/or transverse thickness. The differing physical size of the compartments 202 (particularly in terms of thickness) permits the storage of pills/caplets of differing sizes. It also assures the proper ordered arrangement of the compartments 202 within the system 200, as will be described in greater detail later.

The housing 204 that encloses the compartments 202 is mounted in the device 10, behind the drawer 38 that contains the testing devices (see FIGS. 10 and 11). The housing 204 can be tilted out from back of the device 10 for service and to load medication into the system 200 (see FIG. 2 also).

In the illustrated embodiment, as best seen in FIG. 3, the system 200 includes ten separate medication delivery means or mechanisms 206 A through J, one associated with each storage compartment 202. Each mechanism 206 is individually controlled by one of the control elements 50 in response to a prescribed control signal or signals in the manner previously described.

Each delivery mechanism 206 is identical in construction, so only one will be described in detail.

In the illustrated arrangement (as best shown in FIGS. 12 to 15), the medication storage columns 208 are located between a front (right) wall 211 and a rear (left) wall 213 formed within the compartment 202. The lower end 209 of each vertical medication storage column 208 is open. The ends 209 open into a channel 210 that spans the bottom of the compartment 202. The lower edges 215 of the front and rear walls 211 and 213 are closed.

The channel 210 includes an open front end 212 adjacent the compartment's front wall 211 and an open back end 214 adjacent the compartment's rear wall 213 (respectively positioned to the right and to the left in FIGS. 12 to 15). The channel 210 also includes a bottom wall 216 and two upstanding sidewalls 218 (see FIG. 3). The channel bottom wall 216 includes a opening 220 adjacent its open back (left) end 214, directly beneath the closed lower edge 215 of the compartment's rear wall 213.

The delivery mechanism includes a shuttle member 222 that is movable within the channel 210 between a rearward position, fully within the channel 210 (shown in FIG. 12), and a forward position, extending partially outside the open front end 212 of the channel 210 (shown in FIGS. 3 and 14).

Figure 12:
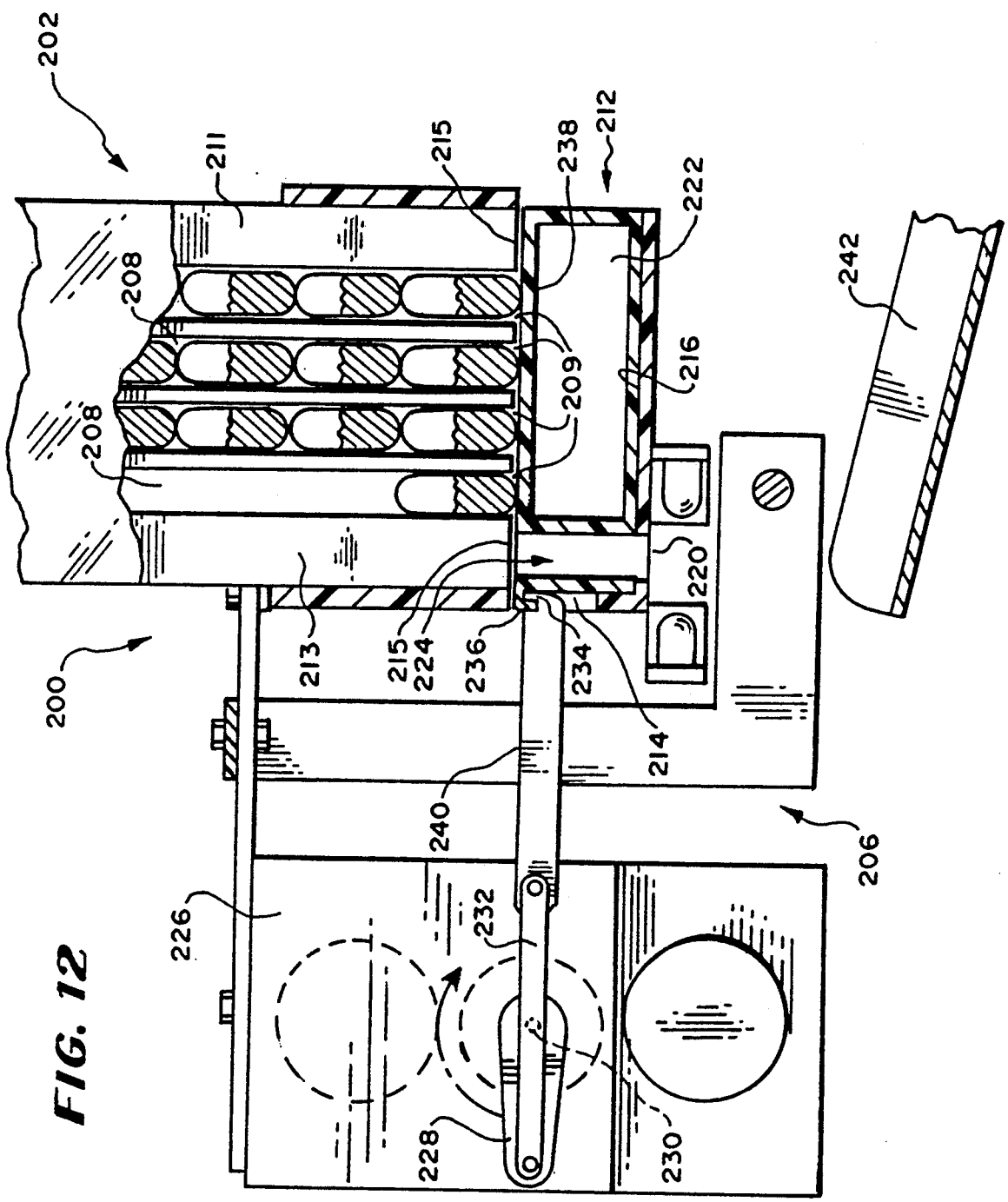
Figure 13:
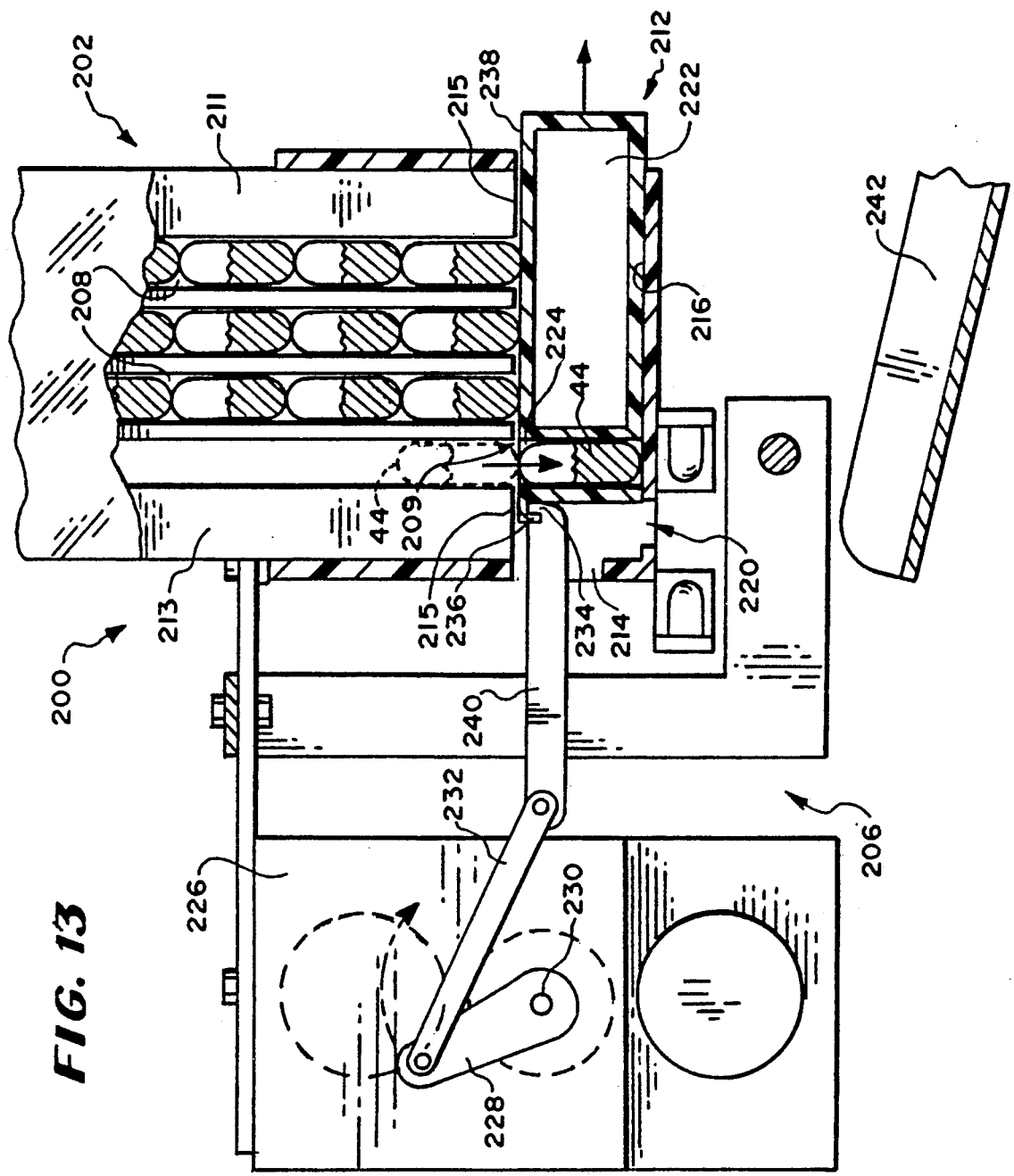

The shuttle member 222 includes an open passageway 224 that registers with the bottom opening 220 in the channel 210 when the shuttle member 222 is in its rearward position (see FIG. 12). Movement of the shuttle member 222 successively toward the forward position (see FIGS. 13 and 14) brings the passageway 224 into sequential registration with the open bottom 209 of each of the storage columns 208.

A linkage assembly couples each shuttle member 222 to an associated electric motor 226 to drive the shuttle member 222 laterally forward and backward within the channel 210. While the construction of the linkage assembly may vary, in the illustrated embodiment, it includes a rotating crank 228 coupled to the drive shaft 230 of the associated motor 226. A double pivoted link 232 is attached at one end to the crank 228. The other end of the double pivoted link 232 includes a hook 234 that attaches to a lip 236 on the end wall of the shuttle member 222.

Rotation of crank 228 thereby imparts forward and rearward pivotal movement to the shuttle member 222. In particular, as shown in FIGS. 12 to 15, one full revolution (360-degrees) of the crank 228 will cycle the shuttle member 222 from its rearward position (FIG. 12) into its forward position (FIG. 14) and back to its rearward position (FIG. 15).

As the shuttle member 222 is moved out toward its forward position (see FIGS. 13 and 14), the passageway 224 will successively come into and out of registry with the bottom 209 of each storage column 208 beginning with the rearwardmost (farthest left) column. The first bottommost pill/caplet encountered in a column will fall by gravity into the empty passageway 224. The closed bottom 216 of the channel 210 retains the fallen pill/caplet within the passageway 224 as the shuttle member 222 moves into is fully forward position and back toward its rearward position (in which the passageway is located beneath the closed lower edge 215 of the compartment's rear wall 213). The presence of the retained pill/caplet prevents another pill/caplet from falling into the passageway 224. Likewise, the leading top wall portion 238 of the shuttle member 222 and the trailing top portion 240 of the link 232 serve to progressively close the bottoms of the other columns as the shuttle member 222 is advanced, preventing additional pills/caplets from entering the channel 210.

When the shuttle member 222 returns to the rearward position (see FIG. 15), the passageway 224 will again register with the bottom channel opening 220. The retained pill/caplet will fall from the passageway 224 through the bottom channel opening 220 and then into a delivery chute 242 that leads to a medication dispenser 244 at the front of the device 10 (see FIG. 3 also).

As shown in FIGS. 1 and 2, the medication dispenser 244 is movable between a closed position (FIG. 1) and an opened position (FIG. 2). A spring 245 (see FIG. 3) normally biases the dispenser 244 toward the opened position, and a solenoid controlled latching mechanism 247 is provided to lock the dispenser 244 in the closed position. At the time medication is released into the delivery chute 242, the dispenser 244 is located in its locked and closed position. Upon delivery of the medication to the dispenser 244, a signal to the latching mechanism 247 allows the dispenser 244 to move into its opened position in response to the bias of the spring 245. The dispensed medication is thereby made available to the patient. Upon taking the medication, the patient closes the dispenser 244, preferably in response to a prompt generated by the device 200.

As in the previously described embodiment, in the illustrated and preferred embodiment of this system (see FIG. 10), each compartment 202 can be individually removed from the housing 204 as a module for replenishment of the medication when the housing 204 is tilted through the back of the device 10. The removable, interchangeable modular design of the compartments 202 simplifies a change in medication brought about by a change in the prescribed medication regime.

Again, it is contemplated that the modular compartments 202 will be prepacked by trained medical or pharmacy personnel at a location away from the device 10 and then carried on site.

In the illustrated arrangement shown in FIG. 10, the motors and linkage assemblies remain in the housing 204 upon removal of the compartments 202. The hooked end 234 of the pivoted link 232 is readily engaged and disengaged from the lip 236 of the associated shuttle member 222.

The system 200 shown in FIGS. 1 to 3 and 10 to 15 includes the separate medication compartments and ten individually controllable delivery mechanisms, one for each compartment. The system 200 can include any one of the control elements 50 shown in FIGS. 6 to 9. The selected control element 50 serves to individually activate the motors 226 associated with each of the compartments 202 by generating different control signals in response to different input criteria in the manner previously described.

For example, if a medication regime requires the administration of three different pills/caplets according to a prescribed schedule, the control element 50 associated with the system 200 can simultaneously generate a first control signal to each of the delivery mechanisms associated with the particular compartments in which the prescribed pills/caplets are located. The three pills/caplets would therefore be dispensed sequentially or at the same time. The control element 50 could dispense other pills/caplets according to different prescribed schedules, or upon patient demands, upon the issuance of appropriate control signals to the other delivery mechanisms.

The system 200 shown in FIGS. 1 to 3 and 10 to 15 is thereby capable of storing and coordinating the administration of many different categories of medication in pill or caplet form in accordance with one or more prescribed schedules, upon demand, or upon any other selected administration criteria.

It should be appreciated that all of the medication delivery systems described in this Specification are applicable for use out of association with a patient monitoring and assistance device. The systems can be used in virtually any environment where storage and delivery of selective medications are desired, such as in a hospital, nursing home, or pharmacy. It should also be appreciated that the medication delivery systems described can be actuated and controlled manually, without reliance upon the automated and highly interactive microprocessor controlled systems described in this Specification. Furthermore, each delivery mechanism and associated storage compartment can be used individually as a single unit, as well as in the multiple configurations shown in this Specification.

The features of the many aspects of the invention are set forth in the following claims.

We claim:

1. A medication delivery device comprising
physical testing means usable for measuring a preselected physical parameter including a testing device for the preselected parameter,
environment testing means for measuring at least one preselected parameter in the user's immediate environment including a sensor for the preselected condition,
medication delivery means for storing at least one dose of medication including a delivery mechanism for making the medication dose available to the user,
control means for comparing the preselected physical parameter measured by the testing device with the preselected environmental parameter measured by the sensor and for generating a first cõmmand signal when a predetermined correlation exists between the two parameters and for generating a second command signal in the absence of the predetermined correlation, and
means for generating a first output in response to the first command signal and for generating a second output, different from the first output, in response to the second command signal, one of the first and second outputs actuating the delivery mechanism to dispense the medication dose.

2. A device according to claim 1
and further including environment control means for changing the preselected environmental parameter, and
wherein one of the first and second outputs actuates the environment control means to change the sensed preselected environmental parameter.

3. A device according to claim 2,
and wherein one of first and second outputs actuates the medication delivery means and the other one of the first and second outputs actuates the environment control means.

4. A device according to claim 1
wherein the testing device measures body temperature,
wherein the sensor measures room temperature, and
wherein the predetermined correlation is a body temperature that is above or below a predetermined level when the sensed room temperature is within prescribed conditions.

5. A user assistance device comprising
a housing,
physical testing means within the housing and usable for measuring a preselected physical parameter, the physical testing means including a testing device for the preselected parameter, the physical testing means being operable in a first mode during which the testing device is retained within the housing away from access and a second mode during which the testing device is made available to the user,
environment testing means for measuring at least one preselected parameter in the user's immediate environment including a sensor for the preselected condition,
input means for receiving and interpreting prescribed commands from the user,
first control means for actuating the physical testing means to shift the operation of the physical testing means from its first mode to its second mode in response to the receipt of interpretation of a prescribed command by the input means, second control means for comparing the preselected physical parameter measured by the testing device with the preselected environmental parameter measured by the sensor and for generating a first command signal when a predetermined correlation exists between the two parameters and for generating a second command signal in the absence of the predetermined correlation, and means for generating a first output in response to the first command signal and for generating a second output, different from the first output, in response to the second command signal.

6. A device according to claim 5 and further including medication delivery means within the housing for storing at least one dose of medication including a delivery mechanism for making the medication dose available to the user, and wherein one of the first and second outputs actuates the delivery mechanism to dispense medication to the user.

7. A device according to claim 5 and further including environment control means within the housing for changing the preselected environmental parameter, and wherein one of the first and second outputs actuates the environment control means to change the sensed preselected environmental parameter.

8. A device according to claim 7 and further including medication delivery means within the housing for storing at least one dose of medication including a delivery mechanism for making the medication dose available to the user, and wherein one of first and second outputs actuates the medication delivery means and the other one of the first and second outputs actuates the environment control means.

9. A device according to claim 5 wherein the input means includes speech recognition means for receiving and interpreting at least one prescribed verbal command made.

10. A user assistance device comprising a housing, medication dispensing means within the housing and being operable in a first mode during which the medication is retained within the housing away from access and in a second mode during which at least one dose of medication is made available to the user, environment testing means for measuring at least one preselected parameter in the user's immediate environment including a sensor for the preselected condition, input means for receiving and interpreting at least one prescribed command from the user relating to a physical condition related to the preselected environmental parameter, first control means for actuating the environmental sensor to measure the predetermined environmental parameter in response to the receipt of interpretation of the prescribed command by the input means and for comparing the sensed measurement with a prescribed value, second control means for generating a first command signal when the sensed environmental measurement compares to the prescribed value and for generating a second command signal when the sensed measurement does not compare to the prescribed value, and means for generating a first output in response to the first command signal and for generating a second output, different from the first output, in response to the second command signal, the medication delivery means being actuated in response to the first output and not in response to the second output.

11. A device according to claim 10 and further including environment control means within the housing for changing the preselected environmental parameter, and wherein one of the second output actuates the environment control means to change the sensed preselected environmental parameter.

12. A device according to claim 10 wherein the input means includes speech recognition means for receiving and interpreting at least one prescribed verbal command made.

13. A medication delivery system comprising a housing, first storage means for storing at least one dose of a medication within the housing away from access by the user, second storage means separate from the first storage means for storing at least one dose of a medication within the housing away from access by the user, first delivery means associated with the first storage means for selectively delivering a medication dose from the first storage means to the user, second delivery means associated with the second storage means for selectively delivering a medication dose from the second storage means to the user, environment testing means for measuring at least one preselected parameter in the user's immediate environment including a sensor for the preselected condition, control means associated with the first and second storage means for actuating the first delivery means in response to a first criteria and for actuating the second delivery means in response to a second criteria different from the first criteria, one of the first and second criteria including, at least in part, a measurement of the preselected environmental parameter.

14. A device according to claim 13 and further including testing means for the user to measure a preselected physical parameter, and wherein one of the first and second criteria includes, at least in part, a measurement of the preselected environmental parameter and a measurement of the preselected physical parameter.

* * * * *